United States Patent
Cai et al.

(10) Patent No.: US 7,348,325 B2
(45) Date of Patent: *Mar. 25, 2008

(54) PYRROLOTRIAZINE KINASE INHIBITORS

(75) Inventors: Zhen-Wei Cai, Belle Mead, NJ (US);
Kyoung S. Kim, North Brunswick, NJ (US); Robert M. Borzilleri, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/605,168

(22) Filed: Nov. 28, 2006

(65) Prior Publication Data

US 2007/0123534 A1    May 31, 2007

Related U.S. Application Data

(60) Provisional application No. 60/740,704, filed on Nov. 30, 2005.

(51) Int. Cl.
| | |
|---|---|
| C07D 487/04 | (2006.01) |
| C07D 471/04 | (2006.01) |
| C07D 401/12 | (2006.01) |
| C07D 403/12 | (2006.01) |
| A61K 31/53 | (2006.01) |
| A61K 31/4427 | (2006.01) |
| A61P 35/00 | (2006.01) |
| A61K 31/506 | (2006.01) |
| A61K 31/519 | (2006.01) |

(52) U.S. Cl. ................... 514/243; 544/183
(58) Field of Classification Search ............... 544/183; 514/243

See application file for complete search history.

(56) References Cited

U.S. PATENT DOCUMENTS

| 5,646,176 A | 7/1997 | Golik et al. |
| 6,214,344 B1 | 4/2001 | Schwall et al. |
| 6,262,094 B1 | 7/2001 | Hoefle et al. |
| 6,750,246 B1 | 6/2004 | Kadow et al. |
| 6,982,265 B1 | 1/2006 | Hunt et al. |
| 2003/0186982 A1 | 10/2003 | Godfrey Jr. et al. |

FOREIGN PATENT DOCUMENTS

| WO | WO99/02514 | 1/1999 |
| WO | WO00/71129 | 11/2000 |
| WO | WO02/40486 | 5/2002 |
| WO | WO03/042172 | 5/2003 |
| WO | WO03/090912 | 11/2003 |
| WO | WO03/091229 | 11/2003 |
| WO | WO2004/054514 | 7/2004 |
| WO | WO2006/004636 A | 1/2006 |

OTHER PUBLICATIONS

Cecil Textbook of Medicine, edited by Bennet, J.C., and Plum F., 20th edition,vol. 1, 1004-1010, 1996.*
Corso et al., Trends in Molecular Medicine, 11(6), 284-292, 2005.*
Kermogrant et al., Cell Cycle 4(3), 352-355, 2005.*
Bardelli, A. et al., "Concomitant activation of pathways downstream of Grb2 and PI 3-kinase is required for *MET*-mediated metastasis", Oncogene, vol. 18, pp. 1139-1146 (1999).
Bottaro, D.P. et al., "Identification of Hepatocyte Growth Factor receptor as the *c-met* Proto-Oncogene Product", Science, vol. 251, pp. 802-804 (1991).
Bussolino, F. et al., "Hepatocyte growth factor is a potent angiogenic factor which stimulates endothelial cell motility and growth", The J. of Cell Biology, vol. 119(3), pp. 629-641 (1992).

(Continued)

*Primary Examiner*—Venkataraman Balasubramanian
(74) *Attorney, Agent, or Firm*—Maureen S. Gibbons; Sammy G. Duncan

(57) ABSTRACT

In general, the instant invention comprises compounds having Formulae I and II:

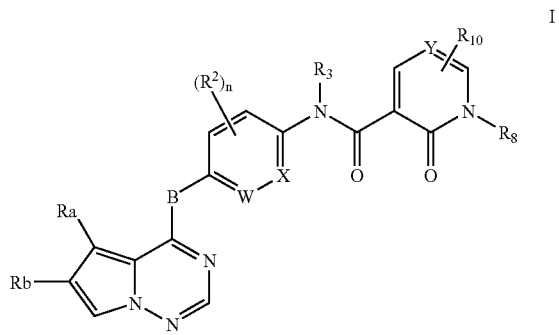

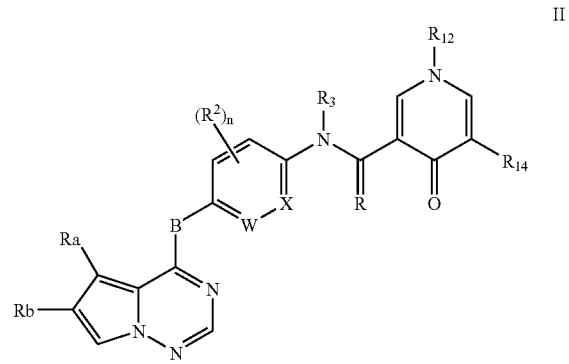

including pharmaceutically acceptable salts thereof. The compounds of the invention are useful as protein kinase inhibitors and therefore are useful for treating cancer and other protein kinase mediated diseases.

8 Claims, No Drawings

OTHER PUBLICATIONS

Camp, R.L. et al., "*Met* expression is associated with poor outcome in patients with axillary lymph node negative breast carcinoma", Cancer, vol. 86(11), pp. 2259-2265 (2000).

Cañibano, V. et al., "Mild regioselective Halogenation of Activated Pyridines with *N*-Bromosuccinimide", Synthesis, vol. 14, pp. 2175-2179 (2001).

Christensen, J. G. et al., "A Selective Small Molecule Inhibitor of c-Met Kinase Inhibits c-Met-Dependent Phenotypes in Vitro and Exhibits Cytoreductive Antitumor Activity in Vivo", Cancer Research, vol. 63, pp. 7345-7355 (2003).

Cooper, C.S. et al., "Amplification and overexpression of the *met* gene in spontaneously transformed NIH3T3 mouse fibroblasts", The EMBO Journal, vol. 5(10), pp. 2623-2628 (1986).

Di Renzo, M. et al., "Overexpression and Amplification of the Met/HGF Receptor Gene during the Progression of Colorectal Cancer[1]", Clinical Cancer Research, vol. 1, pp. 147-154 (1995).

Furge, K. et al., "Met receptor tyrosine kinase: enhanced signaling through adapter proteins", Oncogene, vol. 19, pp. 5582-5589 (2000).

Greene, T., "Protective Groups in Organic Synthesis", Wiley & Sons, Inc. (1991).

Gual, P. et al., "Sustained recruitment of phospholipase C-γ to Gab1 is required for HGF-induced branching tubulogenesis", Oncogene, vol. 19, pp. 1509-1518 (2000).

Hunt, J.T. et al., "Discovery of the Pyrrolo [2,1-*f*] [1,2,4] triazine Nucleus as a New Kinase Inhibitor Template", J. Med. Chem., vol. 47, pp. 4054-4059 (2004).

Jiang, W.G. et al., "Reduction of Stromal Fibroblast-induced Mammary Tumor Growth, by Retroviral Ribozyme Transgenes to Hepatocyte Growth Factor/Scatter Factor and its Receptor, c-MET[1]" Clinical Cancer Research, vol. 9, pp. 4274-4281 (2003).

Kenworthy, P. et al., "The presence of scatter factor in patients with metastatic spread to the pleura", Br. J. Cancer, vol. 66, pp. 243-247 (1992).

Lai, Jui-Fen et al., "Involvement of Focal Adhesion Kinase in Hepatocyte Growth Factor-induced Scatter of Madin-Darby Canine Kidney Cells*", The J. of Biological Chemistry, vol. 275(11), pp. 7474-7480 (2000).

Lee, Jae-Ho et al., "A novel germ line juxtamembrane *Met* mutation in human gastric cancer", Oncogene, vol. 19, pp. 4947-4953 (2000).

Lubensky, I. et al., "Hereditary and Sporadic Papillary Renal Carcinomas with c-*met* Mutations Share a Distinct Morphological Phenotype", American J. of Pathology, vol. 155(2), pp. 517-526 (1999).

Masuya, D. et al., "The tumor-stromal interaction between intratumoral c-Met and stromal hepatocyte growth factor associated with tumor growth and prognosis in non-small-cell lung cancer patients", British J. of Cancer, vol. 90, pp. 1555-1562 (2004).

Matsumoto, K. et al., "Hepatocyte Growth Factor: Molecular Structure, Roles in Liver Regeneration, and Other Biological Functions", Critical Reviews in Oncogenesis, vol. 31(1,2) pp. 27-54 (1992).

Montesano. R. et al., "Identification of a Fibroblast-Derived Epithelial Morphogen as Hepatocyte Growth Factor", Cell, vol. 67, pp. 901-908 (1991).

Park M. et al., "Sequence of *MET* protooncogene cDNA has features characteristic of the tyrosine kinase family of growth-factor receptors", Proc. Natl. Acad. Sci., vol. 84, pp. 6379-6383 (1987).

Rong, S. et al., "Met Proto-oncogene Product is Overexpressed in Tumors of p53-deficient Mice and Tumors of Li-Fraumeni Patients[1]", Cancer Research, vol. 55, pp. 1963-1970 (1995).

Rong, S. et al., "Met Expression and Sarcoma Tumorigenicity", Cancer Research, vol. 53, pp. 5355-5360 (1993).

Sachs, M. et al., "Essential Role of Gab1 for Signaling by the c-Met Receptor In Vivo", The J. of Cell Biology, vol. 150(6), pp. 1375-1384 (2000).

Scarpino, S. et al., "Hepatocyte Growth Factor (HGF) Stimulates Tumour Invasiveness in Papillary Carcinoma of the Thyroid", J. of Pathology, vol. 189, pp. 570-575 (1999).

Schaeper, U. et al., "Coupling of Gab1 to c-Met, Grb2, and Shp2 Mediates Biological Responses", The J. of Cell Biology, vol. 149(7), pp. 1419-1432 (2000).

Soman, N. et al., "The *TPR-MET* oncogenic rearrangement is present and expressed in human gastric carcinoma and precursor lesions", PNAS, vol. 88, pp. 4892-4896 (1991).

Sonnenberg, E. et al., "Scatter Factor/Hepatocyte Growth Factor and Its Receptor, the c-met Tyrosine Kinase, Can Mediate a Signal Exchange between Mesenchyme and Epithelia during Mouse Development", The J. of Cell Biology, vol. 123(1), pp. 223-235 (1993).

Stabile, L.P. et al., "Inhibition of human non-small cell lung tumors by a c-Met Antisense/U6 expression plasmid strategy" Gene Therapy, vol. 11, pp. 3325-3335 (2004).

Stella, M.C. et al., "HGF: a multifunctional growth factor controlling cell scattering", International J. of Biochemistry & Cell Biology, vol. 31, pp. 1357-1362 (1999).

Stoker, M. et al., "Scatter factor is a fibroblast-derived modulator of epithelial cell mobility", Nature, vol. 327, pp. 239-242 (1987).

Stuart, K. et al., "Hepatocyte growth factor/scatter factor-induced intracellular signalling", Int. J. Exp. Path., vol. 81, pp. 17-30 (2000).

Takayama, H. et al., "Diverse tumorigenesis associated with aberrant development in mice overexpressing hepatocyte growth factor/scatter factor", PNAS, vol. 94, pp. 701-706 (1997).

Tanimura, S. et al., "Activation of the 41/43 kDa mitogen-activated protein kinase signaling pathway is required for hepatocyte growth factor-induced cell scattering", Oncogene, vol. 17, pp. 57-65 (1998).

Thibault, C. et al., "Concise and Efficient Synthesis of 4-Fluoro-1*H*-pyrrolo[2,3-*b*] pyridine", Organic Letters, vol. 5(26), pp. 5023-5025 (2003).

\* cited by examiner

PYRROLOTRIAZINE KINASE INHIBITORS

RELATED APPLICATION

This application claims priority benefit under Title 35 § 119(e) of U.S. provisional Application No. 60/740,704, filed Nov. 30, 2005, the contents of which are herein incorporated by reference.

FIELD OF THE INVENTION

This invention relates to compounds that inhibit the protein tyrosine kinase activity of growth factor receptors such as c-Met, thereby making them useful as anti-cancer agents. The pharmaceutical compositions that comprise these compounds are also useful in the treatment of diseases, other than cancer, which are associated with signal transduction pathways operating through growth factor and anti-angiogenesis receptors such as c-Met.

BACKGROUND OF THE INVENTION

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.* 123:223-235, 1993; Matsumato et al., *Crit. Rev. Oncog.* 3:27-54,1992; and Stoker et al., *Nature* 327:239-242, 1987). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell* 67:901-908, 1991), and promotion of invasion (Stella et al., *Int. J. Biochem. Cell Biol.* 12:1357-62, 1999 and Stuart et al., *Int. J. Exp. Path.* 81:17-30, 2000), all critical processes underlying metastasis. HGF has also been reported to promote angiogenesis (Bussolino et al., *J. Cell Biol.* 119:629-641, 1992). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci.* USA 84:6379-83, 1987 and Bottaro et al., *Science* 251:802-4, 1991). The mature form of Met consists of a highly glycosylated external β-subunit as well as a β-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene* 19:5582-9, 2000). These include the p85 subunit of the PI3-kinase, phospholipase Cγ (Gaul et al., *Oncogene* 19:1509-18, 2000), Grb2 and Shc adaptor proteins, the protein phosphatase SHP2 and Gab1. The latter adapter has emerged as the major downstream docking molecule that becomes tyrosine phosphorylated in response to ligand occupancy (Schaeper et al., *J. Cell Biol.* 149:1419-32, 2000; Bardelli, et al., *Oncogene* 18:1139-46, 1999 and Sachs et al., *J. Cell Biol.* 150:1375-84, 2000). Activation of other signaling molecules has been reported in HGF stimulated cells, most notably Ras, MAP kinases, STATs, ERK-1, -2 and FAK (Tanimura et al., *Oncogene* 17:57-65,1998; Lai et al., *J. Biol. Chem.* 275:7474-80 2000 and Furge et al., *Oncogene* 19:5582-9, 2000). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology*, 155:517-26, 1999). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.*, 63:7345-55, 2003; Lee et al., *Oncogene*, 19:4947-53, 2000 and Direnzo et al., *Clin. Cancer Res.*, 1:147-54, 1995). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al. *Cancer Res.* 55:1963-1970, 1995; Rong et al., *Cancer Res.* 53:5355-5360, 1993; Kenworthy et al., *Br. J. Cancer* 66:243-247, 1992 and Scarpino et al. *J. Pathology* 189:570-575, 1999). TPR-Met (an activated form similar to BCR/Abl in CML) has been described and identified in human gastric carcinoma (PNAS 88:4892-6, 1991). In patients with invasive breast carcinoma and in a recent study in non small cell lung cancer patients, expression of either the receptor or ligand is a predictor of decreased survival, further linking Met to tumor progression (Camp et al., *Cancer* 86:2259-65 1999 and Masuya et al., *Br. J. Cancer*, 90:1555-62, 2004). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *PNAS*, 94:701-6, 1997) and an amplified/overexpressed Met spontaneously transforms NIH-3T3 cells (Cooper et al., *EMBO J.*, 5:2623-8, 1986).

Biological agents, such as ribozymes, antibodies and antisense RNA targeting either HGF or Met have been shown to inhibit tumorogenesis (Stabile et al., *Gene Therapy*, 11:325-35, 2004, Jiang et al., *Clin. Cancer Res*, 9:4274-81, 2003 and Genentech U.S. Pat. No. 6,214,344, 2001). Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

SUMMARY

The present invention is directed to compounds having the following Formula I or a salt thereof, or Formula II or a salt thereof:

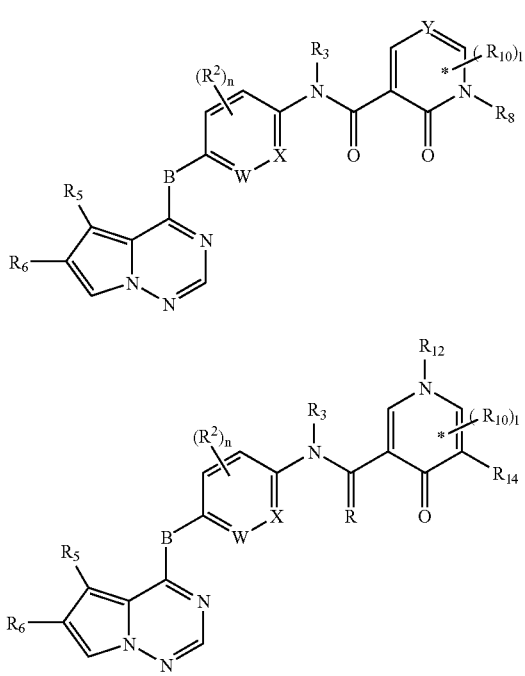

wherein:

each $R^2$ is independently, H, halogen, cyano, $NO_2$, $OR^{15}$, $NR^{16}R^{17}$, $C_1$ to $C_6$ alkyl, substituted $C_1$ to $C_6$ alkyl, $C_3$ to $C_7$ cycloalkyl, substituted $C_3$ to $C_7$ cycloalkyl, a $C_6$ to $C_{14}$ aryl, a substituted $C_6$ to $C_{14}$ aryl, a 5 to 14 membered heteroaryl, a substituted 5 to 14 membered heteroaryl, an aryalkyl, a substituted arylalkyl, a 5 to 14 membered heterocycloalkyl, or a substituted 5 to 14 membered heterocycloalkyl;

B is O, $NR^{18}$, S, SO, $SO_2$, $CR^{19}R^{20}$;

W and X are each independently C or N;

n and l are independently 1 to 4;

p is 0 to 4;

$R^3$ is H or $C_1$ to $C_6$ alkyl;

$R^5$ and $R^6$ are independently, H, halogen, haloalkyl, $NO_2$, cyano, $OR^{26}$, $NR^{27}R^{28}$, $CO_2R^{29}$, $C(O)NR^{30}R^{31}$, $SO_2R^{32}$, $SO_2NR^{33}R^{34}$, $NR^{35}SO_2R^{36}$, $NR^{37}C(O)R^{38}$, $NR^{39}CO_2R^{40}$, —$CO(CH_2)_pR^{41}$, —$CONH(CH_2)_pR^{42}$, —OCONH$(CH_2)_p^{42}$, O-alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;

$R^8$ and $R^{14}$ is $C_6$ to $C_{14}$ aryl, substituted $C_6$ to $C_{14}$ aryl, 5 to 14 membered heteroaryl, or substituted 5 to 14 membered heteroaryl;

each $R^{10}$ is independently H, $C_1$ to $C_6$ alkyl, substituted $C_1$ to $C_6$ alkyl, $C_3$ to $C_7$ cycloalkyl, substituted $C_3$ to $C_7$ cycloalkyl, $C_6$ to $C_{14}$ aryl, substituted $C_6$ to $C_{14}$ aryl, 5 to 14 membered heteroaryl, substituted 5 to 6 membered heteroaryl, 5 to 6 membered heterocycloalkyl, or substituted 5 to 6 membered heterocycloalkyl;

$R^{12}$ is H, alkoxy, $C_1$ to $C_6$ alkyl, substituted $C_1$ to $C_6$ alkyl, $C_3$ to $C_7$ cycloalkyl, substituted $C_3$ to $C_7$ cycloalkyl, $C_6$ to $C_{14}$ aryl, substituted $C_6$ to $C_{14}$ aryl, 5 to 14 membered heteroaryl, substituted 5 to 14 membered heteroaryl, —$CO_2R^{48}$, —$C(O)NR^{49}R^{50}$, $SO_2R^{51}$, $SO_2NR^{52}R^{53}$;

$R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{48}$, $R^{49}$, $R^{50}$, $R^{51}$, $R^{52}$, and $R^{53}$ and are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

The present invention is further directed to methods for treating cancer in a patient in need of such treatment, especially those cancers that are dependent upon Met activation, wherein the Met activation is regulated by gene amplification, an activated Met mutation and/or HGF stimulation, such as bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, MFH/fibrosarcoma, glioblastomas/astrocytomas, melanoma, or mesothelioma.

The present invention is further directed to pharmaceutical compositions comprising compounds having the Formula I or II, as described above, together with a pharmaceutically acceptable carrier.

DESCRIPTION OF THE INVENTION

The present invention is directed to compounds having the following Formula I or II, including pharmaceutically acceptable salts thereof:

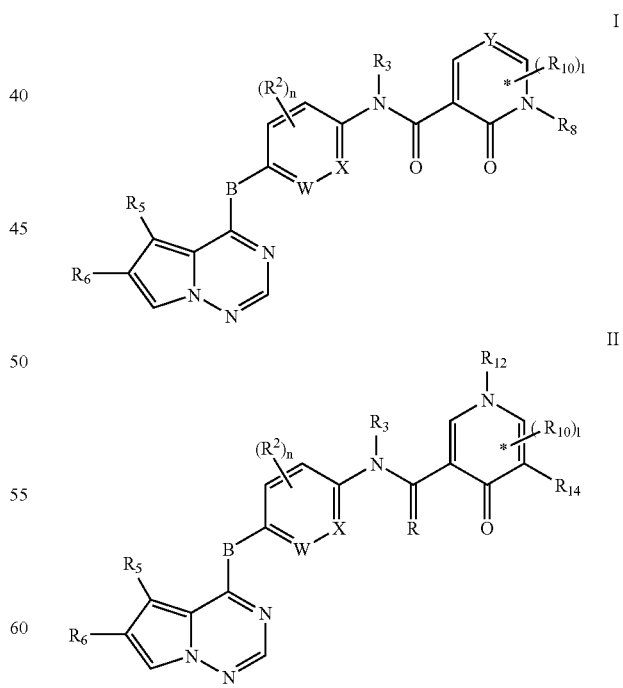

wherein:

each $R^2$ is independently, H, halogen, cyano, $NO_2$, $OR^{15}$, $NR^{16}R^{17}$, $C_1$ to $C_6$ alkyl, substituted $C_1$ to $C_6$ alkyl, $C_3$ to $C_7$ cycloalkyl, substituted $C_3$ to $C_7$ cycloalkyl, a $C_6$ to $C_{14}$ aryl, a substituted $C_6$ to $C_{14}$ aryl, a 5 to 14 membered heteroaryl, a substituted 5 to 14 membered heteroaryl, an aryalkyl, a substituted arylalkyl, a 5 to 14 membered heterocycloalkyl, or a substituted 5 to 14 membered heterocycloalkyl;

B is O, $NR^{18}$, S, SO, $SO_2$, $CR^{19}R^{20}$;

W and X are each independently C or N;

n and 1 are independently 1 to 4;

p is 0 to 4;

$R^3$ is H or $C_1$ to $C_6$alkyl;

$R^5$ and $R^6$ are independently, H, halogen, haloalkyl, $NO_2$, cyano, $OR^{26}$, $NR^{27}R^{28}$, $CO_2R^{29}$, $C(O)NR^{30}R^{31}$, $SO_2R^{32}$, $SO_2NR^{33}R^{34}$, $NR^{35}SO_2R^{36}$, $NR^{37}C(O)R^{38}$, $NR^{39}CO_2R^{40}$, —$CO(CH_2)_pR^{41}$, —$CONH(CH_2)_pR^{42}$, —OCONH$(CH_2)_p^{42}$, O-alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;

$R^8$ and $R^{14}$ is $C_6$ to $C_{14}$ aryl, substituted $C_6$ to $C_{14}$ aryl, 5 to 14 membered heteroaryl, or substituted 5 to 14 membered heteroaryl;

each $R^{10}$ is independently H, $C_1$ to $C_6$ alkyl, substituted $C_1$ to $C_6$ alkyl, $C_3$ to $C_7$ cycloalkyl, substituted $C_3$ to $C_7$ cycloalkyl, $C_6$ to $C_{14}$ aryl, substituted $C_6$ to $C_{14}$ aryl, 5 to 14 membered heteroaryl, substituted 5 to 6 membered heteroaryl, 5 to 6 membered heterocycloalkyl, or substituted 5 to 6 membered heterocycloalkyl;

$R^{12}$ is H, alkoxy, $C_1$ to $C_6$ alkyl, substituted $C_1$ to $C_6$ alkyl, $C_3$ to $C_7$ cycloalkyl, substituted $C_3$ to $C_7$ cycloalkyl, $C_6$ to $C_{14}$ aryl, substituted $C_6$ to $C_{14}$ aryl, 5 to 14 membered heteroaryl, substituted 5 to 14 membered heteroaryl, —$CO_2R^{48}$, —$C(O)NR^{49}R^{50}$, $SO_2R^{51}$, $SO_2NR^{52}R^{53}$;

$R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{48}$, $R^{49}$, $R^{50}$, $R^{51}$, $R^{52}$, and $R^{53}$ and are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

In one embodiment of the present invention, compounds are provided according to Formula I or II wherein Y, W and X are CH.

In one embodiment of the present invention, compounds are provided wherein $R^{10}$ is H.

In one embodiment of the present invention, methods are provided wherein $R^8$ is a phenyl optionally substituted with a halo, such as fluoro.

According to one embodiment of the present invention, pharmaceutical compositions are provided comprising a compound having Formula I or Formula II, as described above, in a pharmaceutically acceptable carrier.

According to one embodiment of the present invention, methods for treating cancer in a patient in need of such treatment are provided, wherein said cancer is dependent upon Met activation, wherein said Met activation is regulated by gene amplification, an activated Met mutation and/or HGF stimulation, comprising administering to said patient a therapeutically effective amount of the compound having Formula I or a salt thereof or Formula II or a salt thereof, as described above.

According to one embodiment of the present invention, the cancer to be treated is selected from bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, MFH/fibrosarcoma, glioblastomas/astrocytomas, melanoma, or mesothelioma.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. Preferred alkyl groups have from 1 to 6 carbon atoms. An alkyl group is an optionally substituted straight, branched or cyclic saturated hydrocarbon group. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). In some preferred embodiments of the present invention, alkyl groups are substituted with, for example, amino, heterocycloalkyl, such as morpholine, piperazine, piperidine, azetidine, hydroxyl, methoxy, or heteroaryl groups such as pyrrolidine.

The term "alkenyl" herein alone or as part of another group refers to a hydrocarbon radical straight, branched or cyclic containing from 2 to 12 carbon atoms and at least one carbon to carbon double bond. Alkenyl groups may also be substituted at any available point of attachment. Exemplary substituents for alkenyl groups include those listed above for alkyl groups, and especially include $C_3$ to $C_7$ cycloalkyl groups such as cyclopropyl, cyclopentyl and cyclohexyl, which may be further substituted with, for example, amino, oxo, hydroxyl, etc.

The term "alkynyl" herein alone or as part of another group refers to a hydrocarbon radical straight, branched or cyclic containing from 2 to 12 carbon atoms and at least one carbon to carbon triple bond. Alkynyl groups may also be substituted at any available point of attachment. Exemplary substituents for alkenyl groups include those listed above for alkyl groups such as amino, alkylamino, etc.

The numbers in the subscript after the symbol "C" define the number of carbon atoms a particular group can contain. For example "$C_1$ to $C_6$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_1$ to $C_6$ alkyl" can also refer to $C_1$ to $C_6$ alkylene which bridges two groups; examples include propane-1,3-diyl, butane-1,4-diyl, 2-methyl-butane-1,4-diyl, etc. "$C_2$ to $C_6$ alkyenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_2$ to $C_6$ alkenyl" can also refer to $C_2$ to $C_6$ alkenediyl which bridges two groups; examples include ethylene-1,2-diyl (vinylene), 2-methyl-2-butene-1,4-diyl, 2-hexene-1,6-diyl, etc. "$C_2$ to $C_6$ alkynyl" means a straight or branched carbon chain having at least one carbon-carbon triple bond, and from two to six carbon atoms; examples include ethynyl, propynyl, butynyl, and hexynyl.

The terms "alkoxy" or "alkylthio" herein alone or as part of another group denote an alkyl group as described above bonded through an oxygen linkage (—O—) or a sulfur linkage (—S—), respectively.

The term "alkoxycarbonyl" herein alone or as part of another group denotes an alkoxy group bonded through a carbonyl group. An alkoxycarbonyl radical is represented by the formula: —C(O)OR, where the R group is a straight or branched $C_{1-6}$ alkyl group, cycloalkyl, aryl, or heteroaryl.

The term "alkylcarbonyl" herein alone or as part of another group refers to an alkyl group bonded through a carbonyl group or —C(O)R.

The term "alkylcarbonyloxy" herein alone or as part of another group denotes an alkylcarbonyl group bonded through an oxygen linkage.

The term "arylalkyl" herein alone or as part of another group denotes an aromatic ring bonded through an alkyl group (such as benzyl) as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, such as Br, F, or Cl, alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol.

The term "amino" herein alone or as part of another group refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —$CO_2H$, —C(=O)H, $CO_2$-alkyl, —C(=O)alkyl, keto, =N—OH, =N—O-alkyl, aryl, heteroaryl, heterocyclo, a five or six membered ketal (i.e. 1,3-dioxolane or 1,3-dioxane), —NR'R", —C(=O) NR'R", —$CO_2$NR'R", —C(=O)NR'R", —NR'$CO_2$R", —NR'C(=O)R", —$SO_2$NR'R", and —NR'$SO_2$R", wherein each of R' and R" are independently selected from hydrogen, alkyl, substituted alkyl, and cycloalkyl, or R' and R" together form a heterocyclo or heteroaryl ring.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —$CO_2H$, —C(=O)H, —$CO_2$-alkyl, —C(=O) alkyl, phenyl, benzyl, phenylethyl, phenyloxy, phenylthio, cycloalkyl, substituted cycloalkyl, heterocyclo, heteroaryl, —NR'R", —C(=O)NR'R", —$CO_2$NR'R", —C(=O) NR'R", —NR'$CO_2$R", —NR'C(=O)R", —$SO_2$NR'R", and —NR'$SO_2$R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyridinonyl, pyrazinyl, pyrimidinyl, pyrimidinonyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocycloalkyl" herein alone or as part of another group refers to a cycloalkyl group (nonaromatic) in which one of the carbon atoms in the ring is replaced by a heteroatom selected from O, S or N, and in which up to three additional carbon atoms may be replaced by said heteroatoms. The term "heterocycloalkyl" herein alone or as part of another group refers to a stable, saturated, or partially unsaturated monocyclic ring system containing 5 to 7 ring members of carbon atoms and other atoms selected from nitrogen, sulfur and/or oxygen. A heterocyclic ring may be a 5, 6 or 7-membered monocyclic ring and contain one, two, or three heteroatoms selected from nitrogen, oxygen and/or sulfur. The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower] alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocycloalkyl groups include piperazine, piperidine, morpholine, homomorpholine, thiomorpholine, pyrrolidine, and azetidine.

A heteroaryl or heterocycloalkyl group may also be an 8-11 membered bicyclic ring which consists of carbon atoms and contains one, two, or three heteroatoms selected from nitrogen, oxygen and/or sulfur. Some preferred bicyclic rings include benzodioxole, quinoxaline, indolyl, and quinolinyl. The term "optionally substituted" as it refers to "heter0aryl" or heterocycloalkyl herein indicates that the heterocyclyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

The term "anticancer" agent includes any known agent that is useful for the treatment of cancer including 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, chlorotrianisene, Hydroxyprogesterone, Aminoglutethimide, Estramustine, Medroxyprogesteroneacetate, Leuprolide, Flutamide, Toremifene, Zoladex, matrix metalloproteinase inhibitors, VEGF inhibitors, including as anti-VEGF antibodies such as Avastin, and small molecules such as ZD6474 and SU6668, vatalanib, BAY-43-9006, SU11248, CP-547632, and CEP-7055 are also included. Anti-Her2 antibodies from Genentech (such as Herceptin) may also be utilized. Suitable EGFR inhibitors include gefitinib, erlotinib, and cetuximab. Pan Her inhibitors include canertinib, EKB-569, and GW-572016. Also included are Src inhibitors, dasatinib (BMS-354825) as well as Casodex® (bicalutamide, Astra Zeneca), Tamoxifen, MEK-1 kinase inhibitors, MAPK kinase inhibitors, PI3 inhibitors, and PDGF inhibitors, such as imatinib. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kinases, and inhibitors of integrin signaling. Additional anticancer agents include microtubule-stabilizing agents such as paclitaxel (also known as Taxol®), docetaxel (also known as Taxotere®), 7-O-methylthiomethylpaclitaxel (disclosed in U.S. Pat. No. 5,646,176), 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Ser. No. 09/712,352 filed on Nov. 14, 2000), C-4 methyl carbonate paclitaxel, epothilone A, epothilone B, epothilone C, epothilone D, desoxyepothilone A, desoxyepothilone B, [1S-[1R*,3R*(E),7R*,10S*,11R*, 12R*,16S*]]-7-11-dihydroxy-8,8,10,12,16-pentamethyl-3-[1-methyl-2-(2-methyl-4-thiazolyl)ethenyl]-4-aza-17 oxabicyclo [14.1.0]heptadecane-5,9-dione (disclosed in WO 99/02514), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione (disclosed in U.S. Pat. No. 6,262,094) and derivatives thereof; and microtubule-disruptor agents. Also suitable are CDK inhibitors, an antiproliferative cell cycle inhibitor, epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Additional cytotoxic agents include, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

As used herein, the term "patient" encompasses all mammalian species.

The phrase "pharmaceutically acceptable salt(s)", as used herein, unless otherwise indicated, includes salts of acidic or basic groups which may be present in the compounds of Formula I or II. The compounds of Formula I or II or II that are basic in nature are capable of forming a wide variety of salts with various inorganic and organic acids. The acids that may be used to prepare pharmaceutically acceptable acid addition salts of such basic compounds of Formula I or II are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

In another embodiment of the invention, a method is provided for treating a proliferative disease via modulation of Met kinase by administering to a patient in need of such treatment an effective amount of a compound of Formula I or II or II, as defined above, in combination (simultaneously or sequentially) with at least one other anti-cancer agent. In a preferred embodiment, the proliferative disease is cancer.

The invention further provides pharmaceutical compositions comprising compounds having Formula I or II together with a pharmaceutically acceptable carrier.

The compounds of Formulas I and II are useful in the treatment of a variety of cancers, including, but not limited to, the following:

a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

c) hematopoietic tumors of myeloid lineage, including acute and chronic myelogenous leukemias, myelodysplastic syndrome and promyelocytic leukemia;

d) tumors of mesenchymal origin, including fibrosarcoma and rhabdomyosarcoma;

e) tumors of the central and peripheral nervous system, including astrocytoma, neuroblastoma, glioma and schwannomas; and f) other tumors, including melanoma, seminoma, teratocarcinoma, osteosarcoma, xenoderoma pigmentosum, keratoctanthoma, thyroid follicular cancer and Kaposi's sarcoma.

Although the compounds of the present invention may be useful for treating a variety of cancers, methods of treating the following cancers are preferred: bladder, breast, colorectal, gastric, head and neck, kidney, liver, lung, pancreatic, gall bladder, prostate, MFH/fibrosarcoma, leiomyosarcoma, multiple myeloma, glioblastoma/astrocytomas, and melanoma.

Due to the key role protein kinases in the regulation of cellular proliferation in general, the compounds of the invention could act as reversible cytostatic agents which may be useful in the treatment of any disease process which features abnormal cellular proliferation, e.g., benign prostatic hyperplasia, familial adenomatosis polyposis, neurofibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formulas I and II as modulators of apoptosis, will be useful in the treatment of cancer (including but not limited to those types mentioned herein above), viral infections (including but not limited to herpes virus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmnentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formulas I or II may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula I or II may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula I or II may also be useful in inhibiting tumor angiogenesis and metastasis.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2).

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.TM. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I or II may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I or II are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of Formula I or II may also be administered sequentially with known anticancer or cytotoxic agents when a combination formulation is inappropriate. The invention is not limited in the sequence of administration; compounds of Formula I or II may be administered either prior to or after administration of the known anticancer or cytotoxic agent(s).

Compounds of Formulas I and II may generally be prepared according to the following Schemes. The compounds are synthesized readily using synthetic methods known to one skilled in the art. Tautomers and solvates (e.g., hydrates) of the compounds of Formula I or II are also within the scope of the present invention. Methods of solvation are generally known in the art. Accordingly, the compounds of the instant invention may be in the free or hydrate form, and may be obtained by methods exemplified by the following schemes below.

In general, the desired fused heterocycles can be prepared using the synthetic routes outlined in the following Schemes. The leaving group (Lg), such as a halogen (or triflate) of a heterocycle (A, whereby open positions may be optionally substituted) 1 can be displaced with a commercially available substituted phenol 2 to provide ether 3 (Scheme 1). Groups A-Lg can be prepared according to the general procedures outlined in, for example, Hunt, J. T. et al. WO 00/071129; Hunt, J. T. et al. *J. Med. Chem.* 2004, 47, 4054-4059; Leftheris, K. et al. WO 02/040486; Mastalerz, H. et al. WO 03/042172; Dyckman, A. et al. WO 03/091229; Vite, G. D. et al. WO 04/054514; Thibault, C. et al. *Org. Lett.* 2003, 5, 5023-5025, all of which are incorporated by reference. Reduction of the nitro group of intermediate 3 with, for example either zinc dust and ammonium chloride or Adam's catalyst (platinum(IV) oxide) under catalytic hydrogenation conditions can furnish the aniline 4.

15

Scheme 1

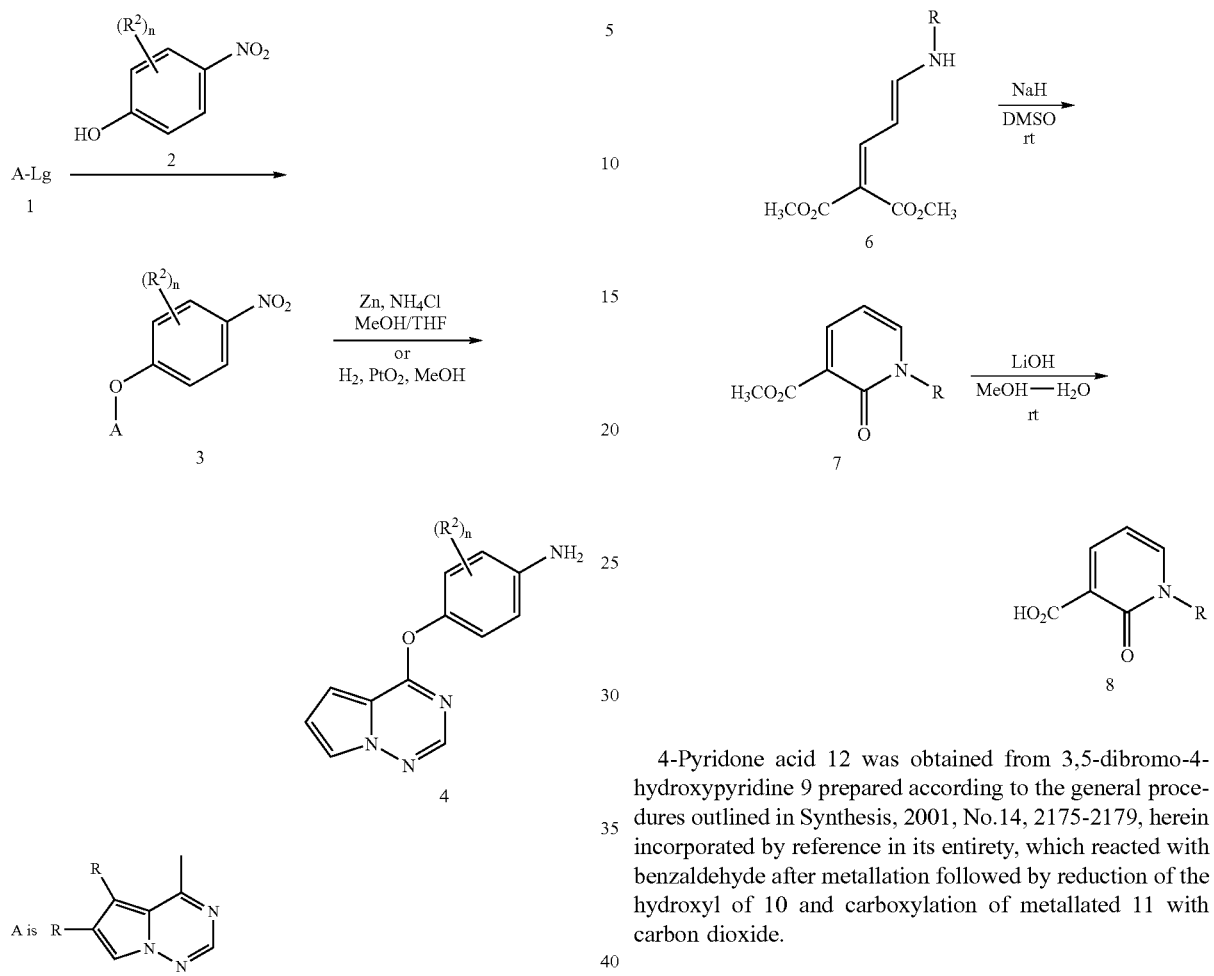

The pyridinone intermediate 7 can be obtained by a two step process beginning with commercially available (E)-dimethyl 2-(3-methoxyallylidene)malonate (5) (Scheme 2). Thus, treatment of compound 5 with an amine or aniline at room temperature can provide intermediate 6, which can then be cyclized in the presence of a base, such as sodium hydride in dimethylsulfoxide to generate 7. Hydrolysis of intermediate 33 under basic conditions can provide the desired pyridinone intermediate 8, which can be coupled to various anilines as described.

16

-continued

4-Pyridone acid 12 was obtained from 3,5-dibromo-4-hydroxypyridine 9 prepared according to the general procedures outlined in Synthesis, 2001, No.14, 2175-2179, herein incorporated by reference in its entirety, which reacted with benzaldehyde after metallation followed by reduction of the hydroxyl of 10 and carboxylation of metallated 11 with carbon dioxide.

Scheme 3

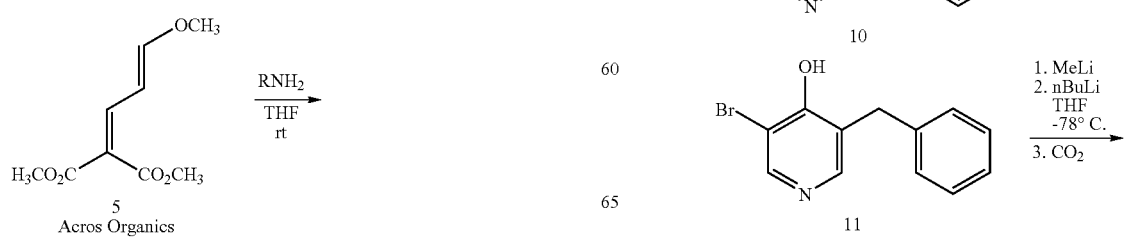

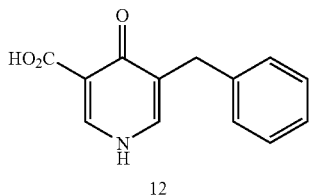

Analogues containing 4-pyridone moiety 16 or 2-pyridinone moiety 17 an be prepared by coupling of the pyridone acids 13 or 14 with any of the anilines defined herein, such as 15, to form 16 or 17.

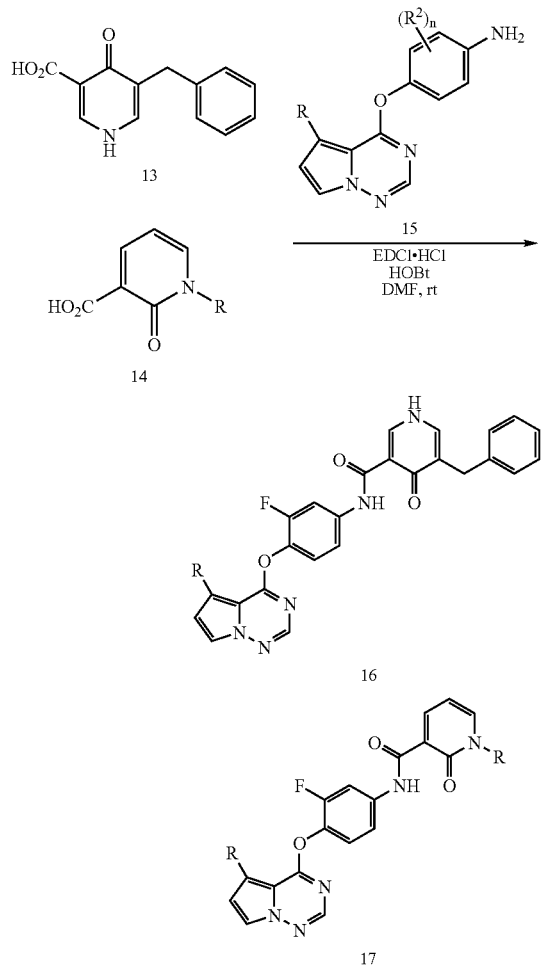

A substituted heterocyclic derivative, for example pyrrolotriazine compound 28 (Scheme 6), can be prepared using the synthetic routes outlined in Schemes 5 and 3. Carboxylic esters, wherein R can be an alkyl or an aryl (such as phenyl) 18 can be contacted with no less than 2 equivalents of an alkyl or aryl organometallic agent such as a Grignard reagent, organolithium, organozinc, etc. to produce the tertiary alcohol 19 (Scheme 5). The reaction is generally performed in an ether solvent, such as tetrahydrofuran, dibutylether, or diethyl ether, or any other non-reactive solvent such as benzene, toluene, or hexane, for example. Tertiary alcohol 19 can be treated with a mixture of acid in the presence of hydrogen peroxide or organic peroxides such as t-butylhydroperoxide, cumenehydroperoxide to affect the rearrangement to hydroxypyrrolotriazine 20. Almost any acid could be used as the catalyst for the oxidative rearrangement, the reaction has been demonstrated with organic acids, mineral acids, and Lewis acids. Some acids which have been used for this type of reaction include: p-toluenesulfonic acid, methansulfonic acid, formic acid, sulfuric acid, nitric acid, $BF_3$-$OEt_2$, trifluoroacetic acid, acidic zeolites, and acidic ion exchange resins. The concentration of the acid can be varied, the concentration and strength of the acid is used to control the kinetics of the reaction. The concentration of the peroxide can be varied from 30-50%. Any reducing agent which reacts to decompose hydrogen peroxide could be used in the quenching of this reaction, including, but not limited to sodium metabisulfite, sodium hydrogen sulfite, sodium thiosulfate, sodium hydrosulfite. A variety of bases can be used while quenching the reaction to control the pH. Hydroxypyrrolotriazine 20 can be reacted with a variety of acylating reagents, to furnish 21 (where, for example, P can be pivalate ester). Compound 21 can be contacted with an appropriate halogenating agent (for example, phosphorous oxychloride, $POCl_3$) to afford 22 (L=Cl). Other reagents can be used to accomplish this transformation besides $POCl_3$, including $PCl_5$, mixtures of $PCl_5$/$POCl_3$, $PhP(O)Cl_2$, $SOCl_2$. Usually an amine is used to catalyze the reaction, including $Et_3N$, $PhNMe_2$, DABCO, etc. Additionally, formamides such as, for example N,N-dimethylformamide and alkylamides such as N-methylpyrrolidinone can also be used to catalyze the reaction. The reaction can be run in any solvent inert to the halogenating agent, including benzene, toluene, THF, etc.

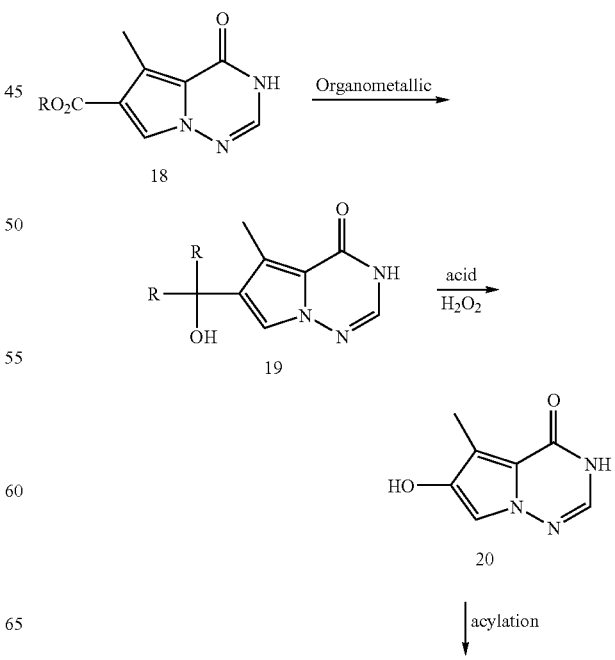

-continued

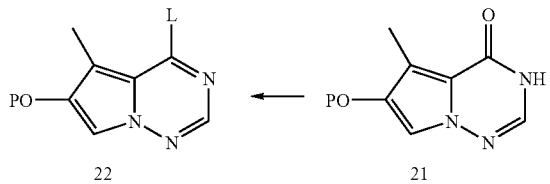

L = Leaving Group
P = Protecting Group
R = Alkyl or Aryl

The appropriately protected imidate 23 (Scheme 6) can be treated with an optionally substituted phenol 2 to provide intermediate 24. Phenol 25, derived from deprotection of compound 24 (using sodium hydroxide in the case where P=pivalate) can be converted to ether 26 via a Mitsunobu reaction with an alcohol. Reduction of the nitro substituent of 26 using the same conditions described above in Scheme 1 can furnish the aniline 27. The desired amine 28 is then furnished by coupling the pyridine acid 8 with aniline 27.

Scheme 6

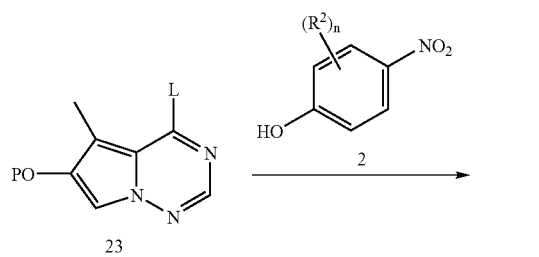

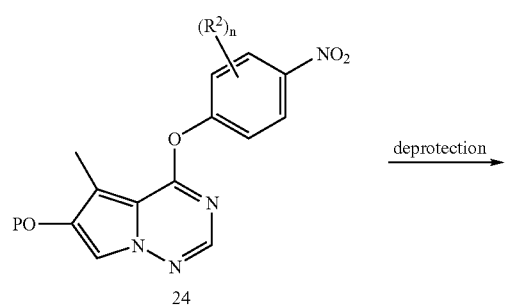

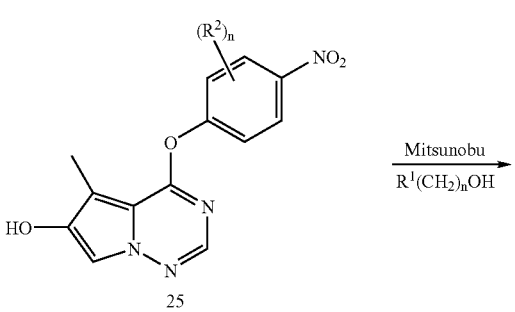

-continued

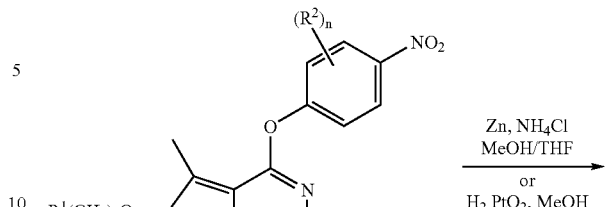

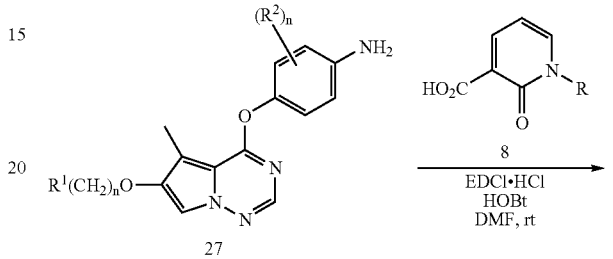

$R^1(CH_2)_nOH$ = any alcohol, but for example:
n = 2-4
$R^1$ = $N(CH_3)_2$, morpholine, N—Me piperazine, etc Various substituents, such as optionally substituted aryl, heteroaryl or vinyl groups can be introduced onto the 5-position of the pyrrolo[2,1-f][1,2,4]triazine ring using the chemistry outlined in Scheme 7. The aminopyrrole derivative 29 can be cyclized in the presence of formamide to produce 5-chloropyrrolo[2,1-f][1,2,4]triazin-4(3H)-one (30). Treatment of intermediate 30 with $POCl_3$ in the presence of a base, such as Hunig's base at elevated temperatures can afford 4,5-dichloropyrrolo[2,1-f][1,2,4]triazine (31). The coupling of an appropriately substituted phenol 2 with compound 31 in the presence of a base, such as potassium carbonate can provide intermediate 32. The nitro group of 32 can be reduced using zinc dust and ammonium chloride to generate the aniline 33. Palladium-mediated coupling reactions with various boronic acids can provide intermediate 34, which can be converted to the desired compounds using chemistry described above.

Scheme 7

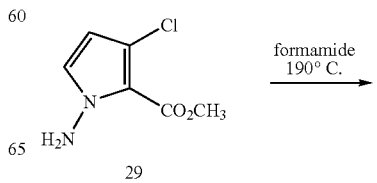

-continued

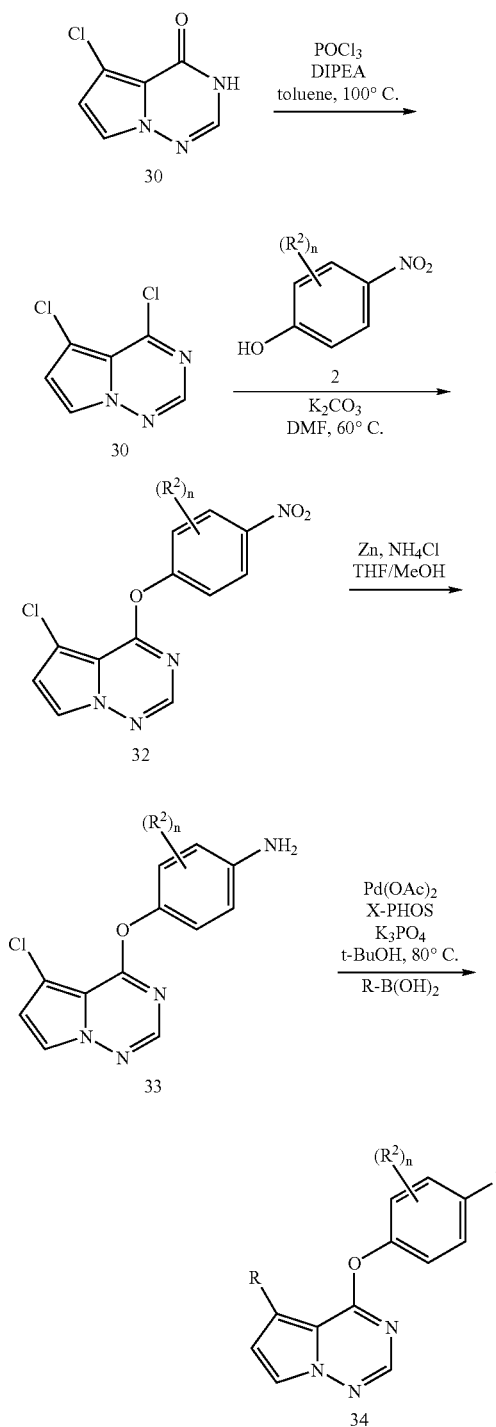

R = aryl, heteroaryl, vinyl

Substitution at the 5-position of the pyrrolo[2,1-f][1,2,4]triazine ring can also be accomplished by coupling the triethylammonium salt 35 with an appropriately substituted phenol 2 followed by treatment with an amine (HNR'R") in the presence of a base, such as Hunig's base to afford the aniline 36 (Scheme 8).

Scheme 8

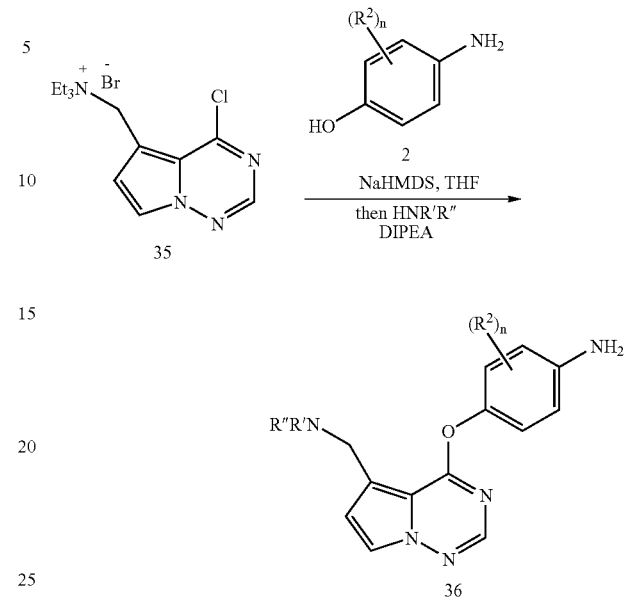

Alternatively, 5-methyl-4-(methylthio)pyrrolo[2,1-f][1,2,4]triazine (27) can be brominated with, for example N-bromosuccinimide (NBS) and 2,2-azobisisobutyronitrile (AIBN) in carbontetrachloride at elevated temperatures (Scheme 9). Treatment of the bromide intermediate with an amine (HNR'R") in the presence of a base, such as Hunig's base can provide intermediate 38. Oxidation of the thiomethyl group of 38 can be accomplished with, for example 3-chloroperbenzoic acid (m-CPBA). Treatment of the sulfone intermediate with the phenoxide generated from compound 2 and sodium bis(trimethylsilyl)amide (NaHMDS) can provide the aniline intermediate 39.

Scheme 9

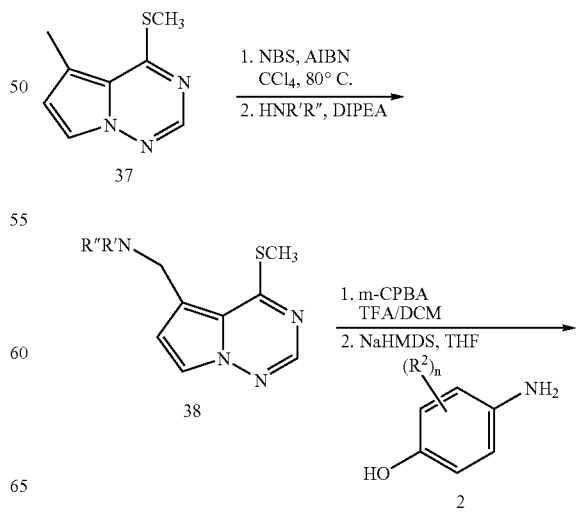

-continued

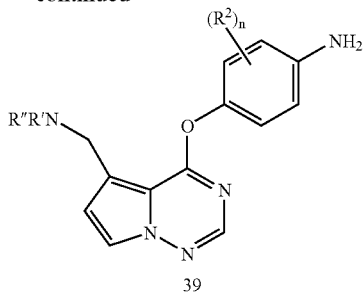

39

The following examples and preparations describe the manner and process of making and using the invention and are illustrative rather than limiting. It should be understood that there may be other embodiments which fall within the spirit and scope of the invention as defined by the claims appended hereto.

Assays

The pharmacological properties of the compounds of this invention may be confirmed by a number of pharmacological assays. The exemplified pharmacological assays which follow have been carried out with the compounds according to the invention and/or their pharmaceutically acceptable salts.

Met Kinase Assay

| Reagents | Substrate Mix Final Concentration |
|---|---|
| Stock Solution | |
| Tris-HCl, (1 M, pH 7.4) | 20 mM |
| $MnCl_2$ (1 M) | 1 mM |
| DTT(1 M) | 1 mM |
| BSA (100 mg/ml) | 0.1 mg/ml |
| polyGlu$_4$/tyr (10 mg/ml) | 0.1 mg/mL |
| ATP (1 mM) | 1 μM |
| γ-ATP (10 μCi/μl) | 0.2 μCi/ml |
| Buffer | Enzyme mix |
| 20 ul 1 M DTT | 4 ul GST/Met enzyme (3.2 mg/ml) = 10 ng/rxn |
| 200 ul 1 M Tris-HCL, pH 7.4 | qs 12 ml Buffer |
| 20 ul 100 mg/ml BSA | |
| qs 20 ml $H_2O$ | |

Incubation mixtures employed for the Met kinase assay contain the synthetic substrate polyGlu:Tyr, (4:1), ATP, ATP-γ-$^{33}$P and buffer containing $Mn^{++}$ and/or $Mg^{++}$, DTT, BSA, and Tris buffer. Reactions are incubated for 60 minutes at 27° C. and stopped by the addition of cold trichloroacetic acid (TCA) to a final concentration 4%. TCA precipitates are collected onto GF/C unifilter plates (Packard Instrument Co., Meriden, Conn.) using a Filtermate universal harvester (Packard Instrument Co., Meriden, Conn.) and the filters are quantitated using a TopCount 96-well liquid scintillation counter (Packard Instrument Co., Meriden, Conn.). Dose response curves are generated to determine the concentration required to inhibit 50% of kinase activity ($IC_{50}$). Compounds are dissolved at 10 mM in dimethyl sulfoxide (DMSO) and evaluated at six concentrations, each in quadruplicate. The final concentration of DMSO in the assay is 1%. $IC_{50}$ values are derived by non-linear regression analysis and have a coefficient of variance (SD/mean, n=6)=16%.

The compounds of the invention inhibit the Met kinase enzyme with $IC_{50}$ values between 0.01 to 100 μM. Preferred compounds have $IC_{50}$ values less than 1.0 μM, and more preferably, less than about 0.5 μM.

The following examples and preparations describe the manner and process of making and using the invention and are illustrative rather than limiting. It should be understood that there may be other embodiments which fall within the spirit and scope of the invention as defined by the claims appended hereto.

EXAMPLES

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

Analytical Reverse Phase (RP) HPLC was performed using a Phenomenex Luna C18 S5 4.6mm×50 mm column or a YMC S5 ODS 4.6×50 mm column. In each case a 4 min linear gradient (from 100% A: %0 B to 0% A: 100% B) was used with the following mobile phase system: A=90% $H_2O$/MeOH+0.2% $H_3PO_4$; B=90% MeOH/$H_2O$+0.2% $H_3PO_4$ at flow rate=4 mL/min and detection at 220 nm.

Preparative Reverse Phase (RP) HPLC was performed with a linear gradient elution using $H_2O$/MeOH mixtures buffered with 0.1% trifluoroacetic acid and detection at 220 nm on one of the following columns: Shimadzu S5 ODS-VP 20×100 mm (flow rate=9 mL/min), or YMC S10 ODS 50×500 mm (flow rate=50 mL/min), or YMC S10 ODS 30×500 mm (flow rate=20 mL/min).

All final products were characterized by $^1$H NMR, RP HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

The following abbreviations are used for commonly used reagents: Boc or BOC: t-butyl carbamate; Fmoc: 9H-fluorenylmethyl carbamate; NMM: N-methylmorpholine; Ms: methanesulfonyl; DIEA or DIPEA: diisopropylethylamine or Hunig's base; NMP: N-methylpyrrolidinone; BOP reagent: benzotriazol-1-yloxytris(trimethylamino)phosphonium hexafluorophosphate; DCC: 1,3-dicyclohexylcarbodiimide; EDCI: 1-(dimethylaminopropyl)-3-ethylcarbodiimide hydrochloride; RT: room temperature; $t_R$: retention time; h: hour(s); min: minute(s); PyBrOP: bromotripyrrolidinophosphonium hexafluorophosphate; TBTU: O-(1H-benzotriazol-1-yl)-N,N,N',N'-tetramethyluronium tetrafluoroborate; DMAP: 4-N,N-dimethylaminopyridine; HOBt: hydroxybenzotriazole; HATU: O-(7-azabenzotriazol-1-yl)-N,N,N',N'-tetramethyluronium hexafluorophosphate; DIBAL-H: diisobutylaluminum hydride; $Na(OAc)_3BH$: sodium triacetoxyborohydride; HOAc: acetic acid; TFA: trifluoroacetic acid; LiHMDS: lithium bis(trimethylsilyl)

amide; m-CPBA: m-chloro: 3-chloroperbenzoic acid; AIBN: 2,2-azobisisobutyronitrile; DMSO: dimethyl sulfoxide; MeCN: acetonitrile; MeOH: methanol; EtOAc: ethyl acetate; DMF: dimethyl formamide; THF: tetrahydrofuran; DCE: 1,2-dichloroethane; Et$_2$O: diethyl ether.

Example 1

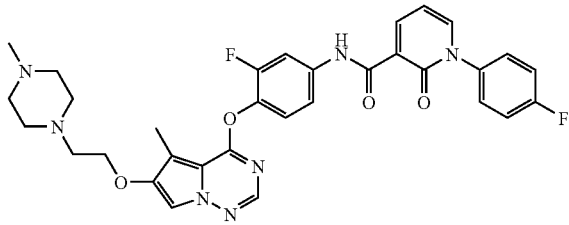

N-(3-Fluoro-4-(5-methyl-6-(2-(4-methylpiperazin-1-yl)ethoxy)pyrrolo[2,1-f][1,2,4]triazin-4-yloxy)phenyl)-1-(4-fluorophenyl)-2-oxo-1,2-dihydropyridine-3-carboxamide

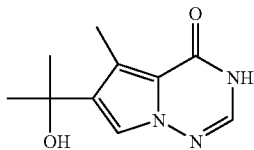

A) 6-(1-Hydroxy-1-methyl-ethyl)-5-methyl-3H-pyrrolo[2,1-f][1,2,4]triazin-4-one

A mixture of 1.9 kg of 5-methyl-4-oxo-3,4-dihydro-pyrrolo[2,1-f][1,2,4]triazine-6-carboxylic acid ethyl ester, prepared generally according to the procedures described in, U.S. patent application Ser. No. 09/573829, herein incorporated by reference in its entirety, and 17.9 kg of THF was prepared under an inert atmosphere and cooled to −10° C. To this mixture was added 14.2 kg methylmagnesium chloride as a 3 M solution in THF at a rate to maintain the reaction temperature <35° C. The reaction mixture was held at 25-45° C. until complete, then cooled to 0° C. A solution of 9.9 kg ammonium chloride in 36.7 kg water was prepared and cooled to 5° C. The organic reaction mixture was added to the ammonium chloride solution at a rate to maintain the internal temperature <15° C. The phases were allowed to settle and the lower aqueous phase drained off and re-extracted with 9.5 kg additional THF. To the combined organic phases was added 8.6 kg EtOAc and the mixture washed with 7.6 kg of saturated aqueous sodium chloride solution. The reaction mixture was filtered, then solvent was removed in vacuo (temperature <40° C.) to about ⅓ the original volume. Additional EtOAc was added with continuing distillation until the THF level was <7%. The resulting slurry was cooled to 0-5° C., then the solid collected by filtration. The wet cake was washed with cold (−10° C.) EtOAc, then dried in vacuo at 40° C. to produce 1.5 kg 6-(1-hydroxy-1-methyl-ethyl)-5-methyl-3H-pyrrolo[2,1-f][1,2,4]triazin-4-one with a purity of 96-99%.

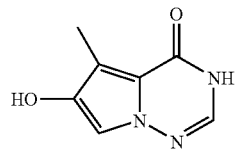

B) 6-Hydroxy-5-methyl-3H-pyrrolo[2,1-f][1,2,4]triazin-4-one

A one liter, 3-neck, round bottom flask as equipped with mechanical stirrer and a cooling bath of ice/acetone. To this was charged 20 g of 6-(1-hydroxy-1-methyl-ethyl)-5-methyl-3H-pyrrolo[2,1-f][1,2,4]triazin-4-one, 235 mL of THF and 47 mL 50% aqueous hydrogen peroxide. An exotherm from −7° C. to 7.3° C. was observed and the mixture became a solution. To this was added a pre-cooled solution of 28.5 mL water and 63 mL methanesulfonic acid over 40 min, keeping the temperature between −5° C. and −0.7° C. The solution was stirred at −2° C. for 95 min until HPLC indicated reaction was complete; reaction mixture was quenched, while keeping it at −2° C., by adding it portion wise to a cooled solution of 28.5 mL water, 89 g NaHSO$_3$ and 128 mL 28% aqueous ammonium hydroxide over 40 min, at 15° C. to 25° C. The mixture was stirred at room temperature for 20 min; pH was 6.80 and a peroxide test was negative. The layers were separated and the aqueous layer was extracted with 100 mL THF. The two organic layers were combined and concentrated, removing 280 mL solvent. To the thick slurry was added 250 mL water and the concentration continued until 88 mL of solvent was removed. The slurry was filtered and the cake was washed with 25 mL water twice and then 25 mL acetonitrile. It was dried by suction on the filter to constant weight to yield 12.51 g of 6-hydroxy-5-methyl-3H-pyrrolo[2,1-f][1,2,4]triazin-4-one, 75.9% yield, 96.5% purity.

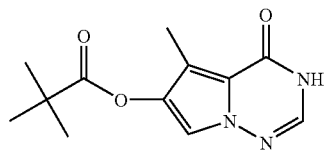

C) 2,2-Dimethyl-propionic acid 5-methyl-4-oxo-3,4-dihydro-pyrrolo[2,1-f][1,2,4]triazin-6-yl ester A mixture of 2.9 kg 6-hydroxy-5-methyl-3H-pyrrolo[2,1-f][1,2,4]triazin-4-one, 4.6 kg of diisopropylethylamine and 17.0 kg of THF was cooled to 0-10° C., then treated with 2.6 kg pivaloyl chloride at a rate to maintain the temperature <20° C. The mixture was stirred until the reaction was complete by HPLC, then 17.8 kg of toluene was added, followed by 20.6 kg of 15% aqueous potassium dihydrogen phosphate solution. The phases were separated and the organic was washed with 10.2 kg water. The organic phase was filtered, then distilled under vacuum with a maximum temperature of 65° C. Additional toluene can be added and distillation continued until the concentration of THF is <8%, and the total reactor volume was reduced to 31 L. The resulting slurry was cooled to 20-25° C. and treated with 20.3 kg heptane over 1.5 h. The slurry was cooled to 0-5° C.

and held for 1 h, then the solid was collected by filtration and dried to yield 4.0 kg of 2,2-dimethyl-propionic acid 5-methyl-4-oxo-3,4-dihydro-pyrrolo[2,1-f][1,2,4]triazin-6-yl ester with a purity of 95-99%.

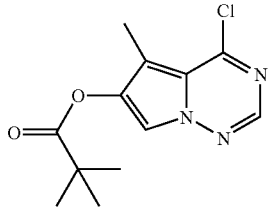

D) 4-Chloro-5-methylpyrrolo[2,1-f][1,2,4]triazin-6-yl pivalate

To a mixture of 5-methyl-4-oxo-3,4-dihydropyrrolo[2,1-f][1,2,4]triazin-6-yl pivalate (300 mg, 1.20 mmol), phosphorus oxychloride (2.0 mL, 21.4 mmol) and DIEA (0.5 mL, 2.80 mmol) was added toluene (10 mL). The reaction was heated at 110° C. for 4 hours and then cooled to room temperature. The mixture was diluted with ethyl acetate (10 mL) and water (5 mL). The organic layer was separated and dried with sodium sulfate, concentrated in vacuo and purified by silica gel flash chromatography (eluted with 1-25% EtOAc/CH$_2$Cl$_2$) to give the title compound (250 mg, 78%) as a white solid.

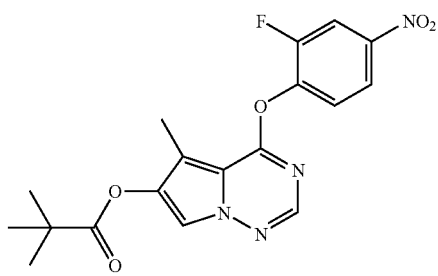

E) 4-(2-Fluoro-4-nitrophenoxy)-5-methylpyrrolo[2,1-f][1,2,4]-triazin-6-yl pivalate To a homogeneous solution of 4-chloro-5-methylpyrrolo[2,1-f][1,2,4]triazin-6-yl pivalate (1.00 g, 3.74 mmol, Compound D of Example 1) and 2-fluoro-4-nitrophenol (588 mg, 3.74 mmol) in anhydrous acetonitrile (25 mL), at room temperature under a nitrogen atmosphere, was added DABCO (462 mg, 4.12 mmol). The mixture was then heated at 50° C. for 3 h. The mixture was cooled to room temperature then partitioned between chloroform and saturated aqueous ammonium chloride. The aqueous layer was extracted twice with chloroform. The combined organic layers were washed once each with saturated aqueous ammonium chloride and saturated aqueous sodium chloride, dried over anhydrous magnesium sulfate and concentrated in vacuo to yield a pale yellow solid that was used in the next step without further purification. MS(ESI$^+$) m/z 389.1 (M+H)$^+$.

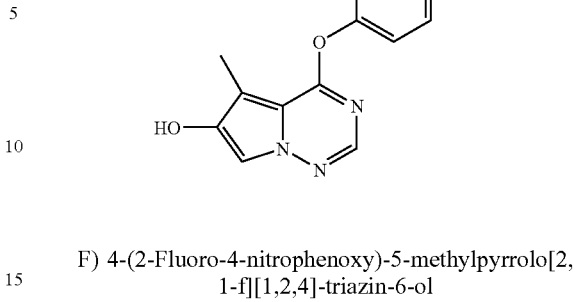

F) 4-(2-Fluoro-4-nitrophenoxy)-5-methylpyrrolo[2,1-f][1,2,4]-triazin-6-ol

To a heterogeneous mixture of 4-(2-fluoro-4-nitrophenoxy)-5-methylpyrrolo[2,1-f][1,2,4]-triazin-6-yl pivalate (1.45 g, 3.74 mmol) in absolute ethanol (19 mL), at room temperature under a nitrogen atmosphere, was added 1 N aqueous sodium hydroxide. The reaction mixture was stirred at ambient temperature for 1.5 h before being neutralized to pH 7 with 1 N aqueous hydrochloride. The reaction mixture was concentrated to remove ethanol, before being partitioned between ethyl acetate and water. The aqueous layer was extracted twice with ethyl acetate. The combined organic extracts were washed twice with water, once with saturated aqueous sodium chloride, dried over anhydrous magnesium sulfate and concentrated in vacuo. Purification by silica gel (Merck KGBA, 230-400 mesh particle size) flash chromatography, eluting with 2:1 hexane/ethyl acetate, afforded the title compound (602 mg, 53% for Steps A-B) as a yellow solid. $^1$H NMR (CDCl$_3$) δ 8.20-8.12 (m, 2H), 7.84 (s, 1H), 7.58-7.53 (m, 1H), 7.53 (s, 1H), 4.76 (s, 1H), 2.48 (s, 3H); MS(ESI$^+$) m/z 305.2 (M+H)$^+$.

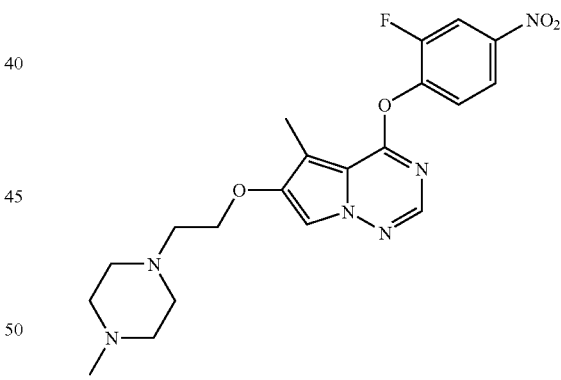

G) 4-(2-Fluoro-4-nitrophenoxy)-5-methyl-6-(2-(4-methylpiperazin-1-yl)-ethoxy)pyrrolo[2,1-f][1,2,4]triazine To a homogeneous mixture of 4-(2-fluoro-4-nitrophenoxy)-5-methylpyrrolo[2,1-f][1,2,4]-triazin-6-ol (100 mg, 0.33 mmol) and triphenylphosphine (129 mg, 0.49 mmol) in 4 mL of 1:1 anhydrous dichlormethane/anhydrous tetrahydrofuran, cooled to 0° C. under a nitrogen atmosphere, was added dropwise a mixture of 2-(4-methylpiperazin-1-yl) ethanol (71 mg, 0.49 mmol) and diisopropylazodicarboxylate (0.10 μL, 0.49 mmol) in 2 mL of 1:1 anhydrous dichlormethane/anhydrous tetrahydrofuran. The mixture was stirred and allowed to warm to room temperature. The reaction was stirred for twelve hours before being concentrated in vacuo. The residue was purified by preparative HPLC (YMC S10 ODS, 30×500 mm, 30 minute gradient from 50% to 90% aqueous methanol with 0.1% TFA). The appropriate fractions were combined, neutralized with saturated aqueous sodium bicarbonate, and then concentrated in vacuo to remove methanol. The mixture was extracted with chloroform (3×10 mL). The combined organic layers were washed once each with water and brine, dried over anhydrous magnesium sulfate, and concentrated in vacuo to yield the title compound (34 mg, 24%) as a yellow solid. $^1$H NMR (CDCl$_3$) δ 8.20-8.10 (m, 2H), 7.82 (s, 1H), 7.58-7.52 (m, 1H), 7.49 (s, 1H), 4.16 (t, 2H, J=5.7 Hz), 2.87 (t, 2H, J=5.7 Hz), 2.80-2.40 (m, 8H), 2.45 (s, 3H), 2.31 (s, 3H); MS(ESI$^+$) m/z 431.3 (M+H)$^+$.

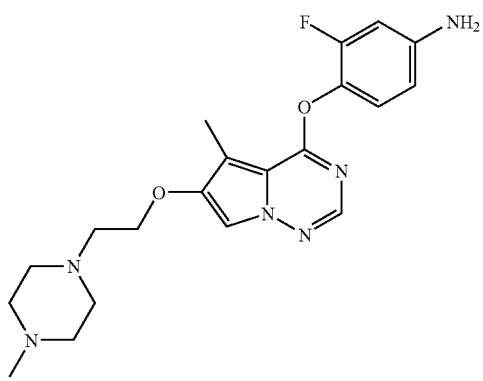

H) 3-Fluoro-4-(5-methyl-6-(2-(4-methylpiperazin-1-yl)ethoxy)pyrrolo[2,1-f]-[1,2,4]triazin-4-yloxy)benzenamine To a mixture of 4-(2-fluoro-4-nitrophenoxy)-5-methyl-6-(2-(4-methylpiperazin-1-yl)ethoxy)pyrrolo[2,1-f][1,2,4]triazine (20 mg, 0.05 mmol) in anhydrous methanol (1 mL) and anhydrous THF (1 mL) at ambient temperature under nitrogen atmosphere was added zinc dust (33 mg, 50 mmol) and ammonium chloride (27 mg, 50 mmol). The reaction mixture was stirred for 7 h before the catalyst was filtered off and the filtrate was concentrated in vacuo to give a solid which was partitioned between chloroform and water. The aqueous phase was extracted twice with chloroform. The combined organic layers were washed with water, dried over anhydrous magnesium sulfate and concentrated in vacuo to give the desired compound (16 mg, 87%) as a solid. $^1$H NMR (CDCl$_3$) δ 7.86-7.83 (m, 1H), 7.50-7.38 (m, 2H), 7.09-7.00 (m, 1H), 6.56-6.45 (m, 1H), 4.14 (t, 2H, J=5.5 Hz), 2.99-2.38 (m, 18H); MS(ESI$^+$) m/z 401.4 (M+H)$^+$.

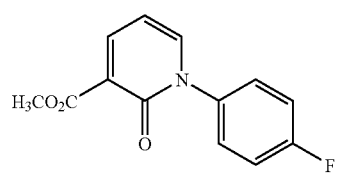

I) Methyl 1-(4-fluorophenyl)-2-oxo-1,2-dihydropyridine-3-carboxylate

To a solution of methyl 2-oxo-2H-pyran-3-carboxylate (2.31 g, 15 mmol, Aldrich) in THF (40 mL) and DMF (10 mL) at rt was added 4-fluoroaniline (1.67 g, 15 mmol), and the reaction mixture was stirred for 2.5 h. To the 4-fluoroaniline intermediate formed via a Michael addition was added EDCI.HCl (3.85 g, 20 mmol) and DMAP (120 mg) at rt. The reaction mixture was stirred at rt overnight. To the reaction mixture were added 1 N aq. HCl (50 mL) and EtOAc (150 mL). The EtOAc layer was separated, and the aqueous layer was washed with EtOAc (150 mL). The combined EtOAc layers were dried over MgSO$_4$ and concentrated in vacuo to obtain a semi-solid material (~4.4 g). The crude product was dissolved in ether (100 mL) and methanol (15 mL), and the solid which formed after stirring was filtered off. The filtrate was concentrated in vacuo to afford the desired product (2.95 g, 80%) as a semi-solid, which was sufficiently pure to use in the next step without further purification. $^1$H NMR (DMSO-d$_6$) δ 8.23 (dd, 1H, J=7.2, 2.2 Hz), 7.57 (dd, 1H, J=6.6, 1.7 Hz), 7.32-7.34 (m, 2H), 7.17 (t, 2H, J=8.8 Hz), 6.32 (t, 1H, J=7.1 Hz), 3.89 (s, 3H); MS(ESI$^+$) m/z 248.2 (M+H)$^+$.

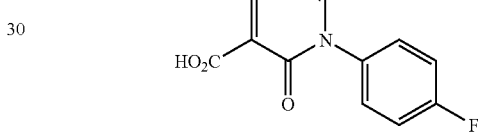

J) 1-(4-Fluorophenyl)-2-oxo-1,2-dihydropyridine-3-carboxylic acid

A mixture of methyl 1-(4-fluorophenyl)-2-oxo-1,2-dihydropyridine-3-carboxylate (crude 2.45 g, 12 mmol) and 6 N aq. NaOH (2.5 mL) in methanol (60 mL) was stirred at rt for 4 h. To the reaction mixture was added conc. HCl (1 mL) slowly with stirring at rt. The precipitate which formed was filtered, washed with a small amount water and dried to obtain the desired acid product (2.1 g) as a yellow solid. The filtrate was concentrated in vacuo. The residue was mixed with water (50 mL) and washed with EtOAc (2×130 mL). The EtOAc layers were dried over MgSO$_4$ and concentrated in vacuo. The residue was triturated with a small amount of ether to obtain a 2$^{nd}$ crop of product (195 mg, total 2.30 g, 82%). $^1$H NMR (DMSO-d$_6$) δ 8.47 (dd, 1H, J=7.2, 2.2 Hz), 8.19 (dd, 1H, J=6.6, 1.7 Hz), 7.62-7.60 (m, 2H), 7.42 (t, 2H, J=8.8 Hz), 6.78 (t, 1H, J=7.1 Hz); MS(ESI$^+$) m/z 234.2 (M+H)$^+$.

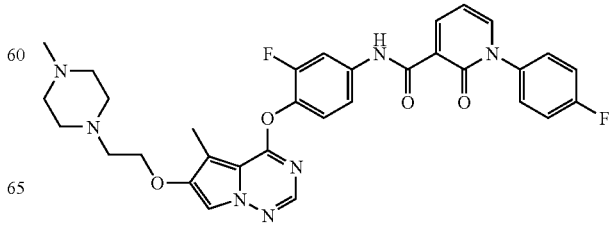

K) N-(3-Fluoro-4-(5-methyl-6-(2-(4-methylpiperazin-1-yl)ethoxy)pyrrolo[2,1-f][1,2,4]triazin-4-yloxy)phenyl)-1-(4-fluorophenyl)-2-oxo-1,2-dihydropyridine-3-carboxamide To a solution of 3-fluoro-4-(5-methyl-6-(2-(4-methylpiperazin-1-yl)ethoxy)pyrrolo[2,1-f][1,2,4]triazin-4-yloxy) benzenamine 30 mg, 0.075 mmol) and 1-(4-fluorophenyl)-2-oxo-1,2-dihydropyridine-3-carboxylic acid in DMF (1.0 mL) at room temperature were added HATU (57 mg, 0.15 mmol, Perspective Biosystem), and DIEA (0.05 mL, 0.3 mmol, Aldrich). The reaction mixture was stirred at rt for 1 h, and was then quenched by the addition of 2 mL of methanol. The reaction mixture was purified by preparative HPLC. The desired fractions were combined, concentrated in vacuo, and neutralized to pH 8 with aq. $K_2HPO_4$. The title compound (30 mg, 64%) was obtained as a white solid which was collected by filtration and dried under vaccum. $^1$H NMR (DMSO-$d_6$) δ 12.09 (br s, 1H), 8.58 (dd, 1H, J=7.15, 2.20 Hz, 1H), 8.12 (dd, 1H, J=6.60, 1.65 Hz), 7.98 (s, 1H), 7.95 (d, 2H, J=3.85 Hz), 7.62-7.59 (m, 2H), 7.45-7.40 (m, 4H), 6.72 (t, 1H, J=9.90 Hz), 4.13 (t, 2H, J=5.5 Hz), 2.71 (d, 2H, J=5.5 Hz), 2.60-2.25 (m, 8H), 2.35 (s, 3H), 2.16 (s, 3H); MS(ESI$^{30}$) m/z 616.40 (M+H)$^+$.

Example 2

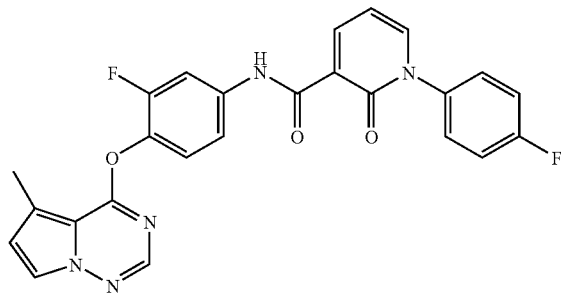

N-(3-Fluoro-4-(5-methylpyrrolo[2,1-f][1,2,4]triazin-4-yloxy)phenyl)-1-(4-fluorophenyl)-2-oxo-1,2-dihydropyridine-3-carboxamide

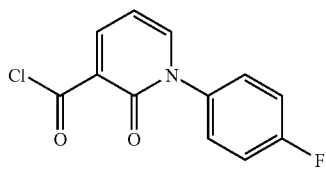

A) 1-(4-Fluorophenyl)-2-oxo-1,2-dihydropyridine-3-carbonyl chloride

To a suspension of 1-(4-fluorophenyl)-2-oxo-1,2-dihydropyridine-3-carboxylic acid) (Compound J of Example 1) 475 mg, 2.04 mmol), was added oxalyl chloride (388 mg, 3 mmol), followed by one drop of DMF. The resulting mixture was stirred at rt for 1 h. The mixture was then concentrated in vacuo to afford the desired compound (500 mg, 100%) as a beige solid, which was used directly in the next step without further purification.

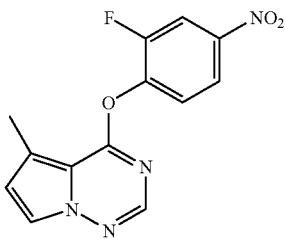

B) 4-(2-Fluoro-4-nitrophenoxy)-5-methylpyrrolo[2,1-f][1,2,4]triazine

To a mixture of 4-chloro-5-methylpyrrolo[2,1-f][1,2,4]triazine (3.37 g, 20.11 mmol, PCT Appl.WO 2000/071129, U.S. pat. application 2003/0186982, the disclosure of which is herein incorporated by reference) and 2-fluoro-4-nitrophenol (3.48 g, 22.12 mmol) in anhydrous DMF (100 mL), stirred for 5 minutes under a nitrogen atmosphere, was added anhydrous potassium carbonate (6.11 g, 44.24 mmol). The mixture was heated at 60° C. for 15 h before 2-fluoro-4-nitrophenol (1.00 g, 6.37 mmol) was added and stirring continued at 60° C. for 4.5 h. The mixture was cooled to room temperature, diluted with dichloromethane, washed sequentially with water and 10% aqueous lithium chloride, dried over anhydrous magnesium sulfate and concentrated in vacuo to yield a tan solid. Purification by silica gel (Merck KGaA, 230-400 mesh particle size) flash chromatography, eluting with chloroform, afforded the title compound (4.19 g, 72%) as a pale yellow solid. $^1$H NMR (CDCl$_3$) δ 8.20-8.13 (m, 2H), 7.83 (s, 1H), 7.73 (d, 1H, J=2.6 Hz); 7.58-7.53 (m, 1H), 6.69 (d, 1H, J=2.4 Hz), 2.62 (s, 3H); HRMS(ESI), 289.0737 (M+H)$^+$ calc, 289.0733 (M+H)$^+$ found.

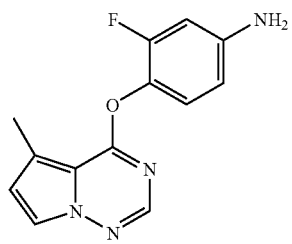

C) 3-Fluoro-4-(5-methylpyrrolo[2,1-f][1,2,4]triazin-4-yloxy)benzenamine

To a heterogeneous mixture of 4-(2-fluoro-4-nitrophenoxy)-5-methylpyrrolo[2,1-f][1,2,4]triazine (3.04 g, 10.55 mmol) in anhydrous methanol (60 mL) and anhydrous tetrahydrofuran (40 mL), at ambient temperature under nitrogen atmosphere, was added zinc dust (6.90 g, 105 mmol) and ammonium chloride (5.64 g, 105 mmol). The mixture was stirred for 7 h before the catalyst was filtered off and the filtrate was concentrated in vacuo to a pale yellow solid which was partitioned between chloroform and water. The aqueous layer was then extracted twice with chloroform. The combined chloroform layers were washed with water, dried over anhydrous magnesium sulfate and concentrated in vacuo to yield the title compound (2.51 g, 92%) as a solid. $^1$H NMR (CDCl$_3$) δ 7.86 (s, 1H), 7.64 (d, 1H, J=2.6 Hz); 7.08-7.03 (m, 1H), 6.61 (d, 1H, J=2.4 Hz), 6.55-6.45 (m, 2H), 3.78 (s, 2H), 2.60 (s, 3H); HRMS(ESI), 259.0995 (M+H)$^+$ calc, 259.0997 (M+H)$^+$ found.

D) N-(3-Fluoro-4-(5-methylpyrrolo[2,1-f][1,2,4]triazin-4-yloxy)phenyl)-1-(4-fluorophenyl)-2-oxo-1,2-dihydropyridine-3-carboxamide To a solution of 3-fluoro-4-(5-methylpyrrolo[2,1-f][1,2,4]triazin-4-yloxy)benzenamine (62 mg, 0.24 mmol) in dichloromethane (2 mL) and pyridine (0.5 mL), was added dropwise a solution of 1-(4-fluorophenyl)-2-oxo-1,2-dihydropyridine-3-carbonyl chloride (30 mg, 0.12 mmol) in dichloromethane (0.5 mL). The reaction mixture was stirred at rt for 30 min, and then concentrated to dryness. The residue was washed with methanol. The solid that formed was collected by filtration and dried under vaccum to give the title compound (35 mg, 61%). $^1$H NMR (DMSO-$d_6$) δ 12.10 (br s, 1H), 8.58 (dd, 1H, J=7.15, 2.20 Hz), 8.12 (dd, 1H, J=6.60, 1.65 Hz), 7.98 (s, 1H), 7.95 (d, 2H, J=2.75 Hz), 7.62-7.58 (m, 2H), 7.40-7.47 (m, 4H), 6.78 (d, 1H, J=2.75 Hz), 6.72 (t, 1H, J=7.15 Hz), 2.54 (s, 3H); MS(ESI$^+$) m/z 474.23 (M+H)$^+$.

What is claimed is:

1. A compound having Formula I or a salt thereof or Formula II or a salt thereof:

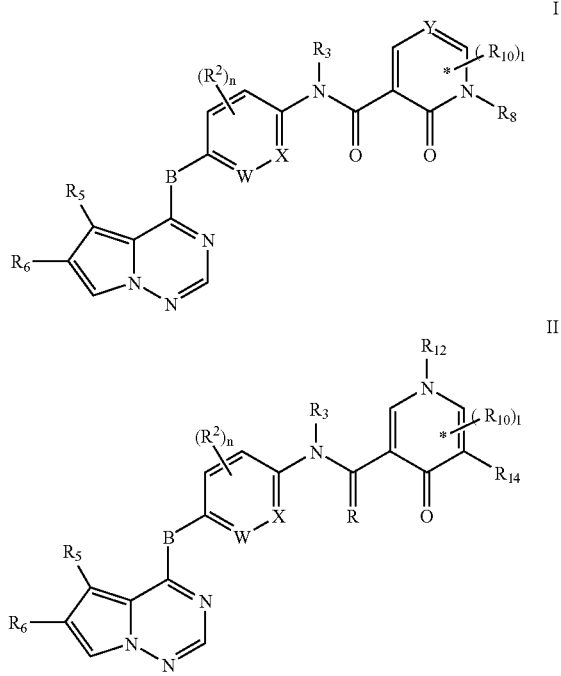

wherein:
R is O;
Y is CH;
each $R^2$ is independently, H, halogen, cyano, $NO_2$, $C_1$ to $C_6$ alkyl, substituted $C_1$ to $C_6$ alkyl, $C_3$ to $C_7$ cycloalkyl, substituted $C_3$ to $C_7$ cycloalkyl, a $C_6$ to $C_{14}$ aryl, a substituted $C_6$ to $C_{14}$ aryl, a 5 to 14 membered heteroaryl, a substituted 5 to 14 membered heteroaryl, an arylalkyl, a substituted arylalkyl, a 5 to 14 membered heterocycloalkyl, or a substituted 5 to 14 membered heterocycloalkyl;
B is O, S, SO, or $SO_2$;
W and X are each independently C or N;
n and l are independently 1 to 4;
p is 0 to 4;
$R^3$ is H or $C_1$ to $C_6$ alkyl;

$R^5$ and $R^6$ are independently, H, halogen, haloalkyl, $NO_2$, cyano, $OR^{26}$, $NR^{27}R^{28}$, $CO_2R^{29}$, $C(O)NR^{30}R^{31}$, $SO_2R^{32}$, $SO_2NR^{33}R^{34}$, $NR^{35}SO_2R^{36}$, $NR^{37}C(O)R^{38}$, $NR^{39}CO_2R^{40}$, —$CO(CH_2)_pR^{41}$, —$CONH(CH_2)_pR^{42}$, —$OCONH(CH_2)_pR^{42}$,
O-alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkenylalkyl, substituted alkenylalkyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;

$R^8$ and $R^{14}$ are independently $C_6$ to $C_{14}$ aryl, substituted $C_6$ to $C_{14}$ aryl, 5 to 14 membered heteroaryl, or substituted 5 to 14 membered heteroaryl;

each $R^{10}$ is independently H, $C_1$ to $C_6$ alkyl, substituted $C_1$ to $C_6$ alkyl, $C_3$ to $C_7$ cycloalkyl, substituted $C_3$ to $C_7$ cycloalkyl, $C_6$ to $C_{14}$ aryl, substituted $C_6$ to $C_{14}$ aryl, 5 to 14 membered heteroaryl, substituted 5 to 6 membered heteroaryl, 5 to 6 membered heterocycloalkyl, or substituted 5 to 6 membered heterocycloalkyl;

$R^{12}$ is H, alkoxy, $C_1$ to $C_6$ alkyl, substituted $C_1$ to $C_6$ alkyl, $C_3$ to $C_7$ cycloalkyl, substituted $C_3$ to $C_7$ cycloalkyl, $C_6$ to $C_{14}$ aryl, substituted $C_6$ to $C_{14}$ aryl, 5 to 14 membered heteroaryl, substituted 5 to 14 membered heteroaryl, —$CO_2R^{48}$, —$C(O)NR^{49}R^{50}$, $SO_2R^{51}$, or $SO_2NR^{52}R^{53}$; and $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{48}$, $R^{49}$, $R^{50}$, $R^{51}$, $R^{52}$, and $R^{53}$ are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

2. The compound according to claim 1 wherein Y, W and X are CH.

3. The compound according to claim 1 wherein $R^{10}$ is H.

4. The compound according to claim 1 wherein $R^8$ is a phenyl optionally substituted with a halo.

5. A compound selected from the group consisting of N-(3-Fluoro-4-(5-methyl-6-(2-(4-methylpiperazin-1-yl)ethoxy)pyrrolo[2,1-f][1,2,4]triazin-4-yloxy)phenyl)-1-(4-fluorophenyl)-2-oxo-1,2-dihydropyridine-3-carboxamide or a salt thereof and N-(3-Fluoro-4-(5-methylpyrrolo[2,1-f][1,2,4]triazin-4-yloxy)phenyl)-1-(4-fluorophenyl)-2-oxo-1,2-dihydropyridine-3-carboxamide or a salt thereof.

6. A pharmaceutical composition comprising a compound having the following Formula I or a salt thereof or Formula II or a salt thereof:

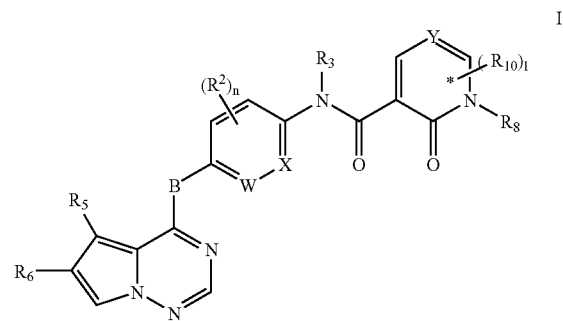

-continued

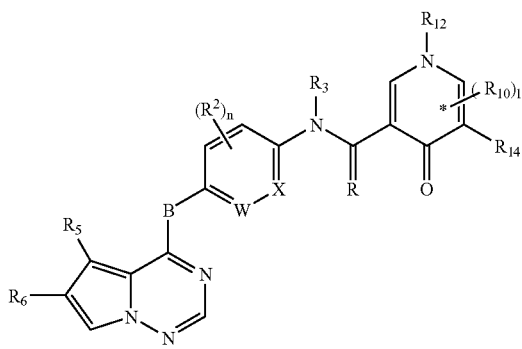

wherein:
R is O:
Y is CH:
each $R^2$ is independently, H, halogen, cyano, $NO_2$, $C_1$ to $C_6$ alkyl, substituted $C_1$ to $C_6$ alkyl, $C_3$ to $C_7$ cycloalkyl, substituted $C_3$ to $C_7$ cycloalkyl, a $C_6$ to $C_{14}$ aryl, a substituted $C_6$ to $C_{14}$ aryl, a 5 to 14 membered heteroaryl, a substituted 5 to 14 membered heteroaryl, an arylalkyl, a substituted arylalkyl, a 5 to 14 membered heterocycloalkyl, or a substituted 5 to 14 membered heterocycloalkyl;
B is O, S, SO, or $SO_2$;
W and X are each independently C or N;
n and 1 are independently 1 to 4;
$R^3$ is H or $C_1$ to $C_6$alkyl;
each $R^{10}$ is independently H, $C_1$ to $C_6$ alkyl, substituted $C_1$ to $C_6$ alkyl, $C_3$ to $C_7$ cycloalkyl, substituted $C_3$ to $C_7$ cycloalkyl, $C_6$ to $C_{14}$ aryl, substituted $C_6$ to $C_{14}$ aryl, 5 to 14 membered heteroaryl, substituted 5 to 6 membered heteroaryl, 5 to 6 membered heterocycloalkyl, or substituted 5 to 6 membered heterocycloalkyl;
$R^{12}$ is H, alkoxy, $C_1$ to $C_6$ alkyl, substituted $C_1$ to $C_6$ alkyl, $C_3$ to $C_7$ cycloalkyl, substituted $C_3$ to $C_7$ cycloalkyl, $C_6$ to $C_{14}$ aryl, substituted $C_6$ to $C_{14}$ aryl, 5 to 14 membered heteroaryl, substituted 5 to 14 membered heteroaryl, -$CO_2R^{48}$, -$C(O)NR^{49}R^{50}$, $SO_2R^{51}$, or $SO_2NR^{52}R^{53}$,
$R^8$ and $R^{14}$ are independently $C_6$ to $C_{14}$ aryl, substituted $C_6$ to $C_{14}$ aryl, 5 to 14 membered heteroaryl, or substituted 5 to 14 membered heteroaryl;
$R^5$ and $R^6$ are independently, H, halogen, $NO_2$, cyano, $OR^{26}$, $NR^{27}R^{28}$, $CO_2R^{29}$, $C(O)NR^{30}R^{31}$, $SO_2R^{32}$, $SO_2NR^{33}R^{34}$, $NR^{35}SO_2R^{36}$, $NR^{37}C(O)R^{38}$, $NR^{39}CO_2R^{40}$, —$CO(CH_2)_rR^{41}$, —$CONH(CH_2)_rR^{42}$, —$OCONH(CH_2)_rR^{42}$, O-alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl; and
$R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{48}$, $R^{49}$, $R^{50}$, $R^{51}$, $R^{52}$, and $R^{53}$ are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

7. A method for treating breast cancer in a patient in need of such treatment wherein said cancer is dependent upon Met activation, wherein said Met activation is regulated by gene amplification, an activated Met mutation and/or HOF stimulation, comprising administering to said patient a therapeutically effective amount of the compound having the following Formula I or a salt thereof or Formula II or a salt thereof:

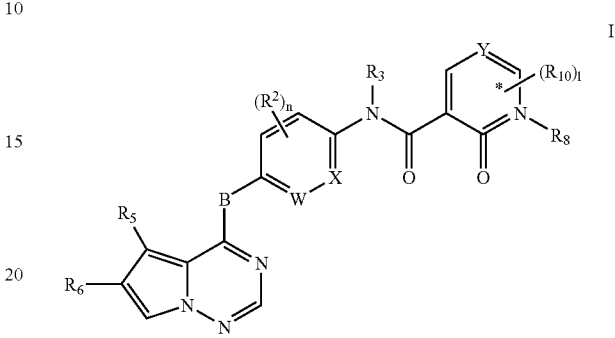

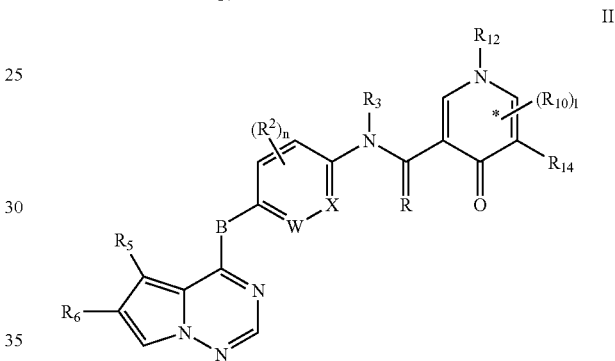

wherein:
R is O:
Y is CH:
each $R^2$ is independently, H, halogen, cyano, $NO_2$, $C_1$ to $C_6$ alkyl, substituted $C_1$ to $C_6$ alkyl, $C_3$ to $C_7$ cycloalkyl, substituted $C_3$ to $C_7$ cycloalkyl, a $C_6$ to $C_{14}$ aryl, a substituted $C_6$ to $C_{14}$ aryl, a 5 to 14 membered heteroaryl, a substituted 5 to 14 membered heteroaryl, an arylalkyl, a substituted arylalkyl, a 5 to 14 membered heterocycloalkyl, or a substituted 5 to 14 membered heterocycloalkyl;
B is O, S, SO, $SO_2$;
W and X are each independently C or N;
n and 1 are independently 1 to 4;
$R^3$ is H or $C_1$ to $C_6$alkyl;
each $R^{10}$ is independently H, $C_1$ to $C_6$ alkyl, substituted $C_1$ to $C_6$ alkyl, $C_3$ to $C_7$ cycloalkyl, substituted $C_3$ to $C_7$ cycloalkyl, $C_6$ to $C_{14}$ aryl, substituted C6 to $C_{14}$ aryl, 5 to 14 membered heteroaryl, substituted 5 to 6 membered heteroaryl, 5 to 6 membered heterocycloalkyl, or substituted 5 to 6 membered heterocycloalkyl;
$R^{12}$ is H, alkoxy, $C_1$ to $C_6$ alkyl, substituted $C_1$ to $C^6$ alkyl, $C_3$ to $C_7$ cycloalkyl, substituted $C_3$ to $C_7$ cycloalkyl, $C_6$ to $C_{14}$ aryl, substituted to $C_6$ to $C_{14}$ aryl, 5 to 14 membered heteroaryl, substituted 5 to 14 membered heteroaryl, -$CO_2R^{48}$, -$C(O)NR^{49}R^{50}$, $SO^2R^{51}$, or $SO_2NR^{52}R^{53}$;
$R^8$ and $R^{14}$ are independently $C_6$ to $C_{14}$ aryl, substituted $C_6$ to $C_{14}$ aryl, 5 to 14 membered heteroaryl, or substituted 5 to 14 membered heteroaryl;

$R^5$ and $R^6$ are independently, H, halogen, $NO_2$, cyano, $OR^{26}$, $NR^{27}R^{28}$, $CO_2R^{29}$, $C(O)NR^{30}R^{31}$, $SO_2R^{32}$, $SO_2NR^{33}R^{34}$, $NR^{35}SO_2R^{36}$, $NR^{37}C(O)R^{38}$, $NR^{39}CO_2R^{40}$, $-CO(CH_2)_iR^{41}$, $-CONH(CH_2)_iR^{42}$, $-OCONH(CH_2)_iR^{42}$, O-alkylaminoalkyl, alkylaminoalkynyl, $C_1$ to $C_6$ alkyl, substituted $C_1$ to $C_6$ alkyl, $C_3$ to $C_7$ cycloalkyl, substituted $C_3$ to $C_7$ cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl; and $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{48}$, $R^{49}$, $R^{50}$, $R^{51}$, $R^{52}$, and $R^{53}$ are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl.

8. The method according to claim 7 further comprising administering to said patient at least one additional anticancer agent.

* * * * *

UNITED STATES PATENT AND TRADEMARK OFFICE
CERTIFICATE OF CORRECTION

PATENT NO. : 7,348,325 B2
APPLICATION NO. : 11/605168
DATED : March 25, 2008
INVENTOR(S) : Cai et al.

It is certified that error appears in the above-identified patent and that said Letters Patent is hereby corrected as shown below:

In Column 33, Lines 25-50,

"
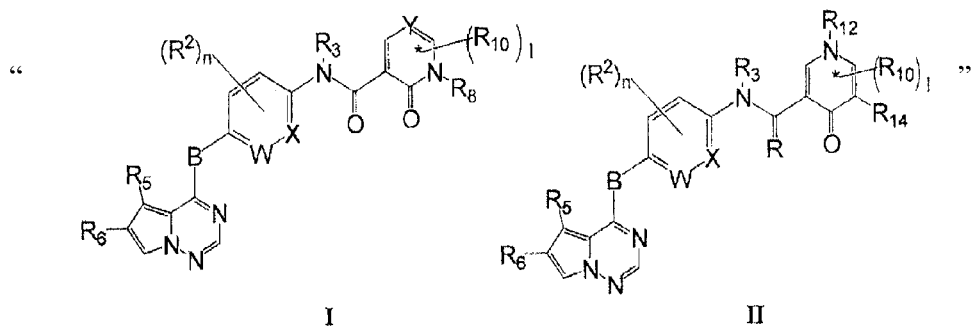
"

should read

--
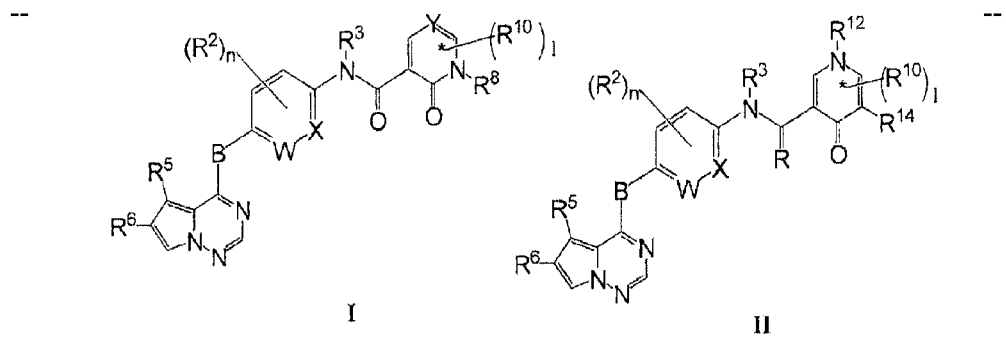
--

UNITED STATES PATENT AND TRADEMARK OFFICE
CERTIFICATE OF CORRECTION

PATENT NO. : 7,348,325 B2  
APPLICATION NO. : 11/605168  
DATED : March 25, 2008  
INVENTOR(S) : Cai et al.

Page 2 of 5

It is certified that error appears in the above-identified patent and that said Letters Patent is hereby corrected as shown below:

In Column 34, Lines 54-67,

"
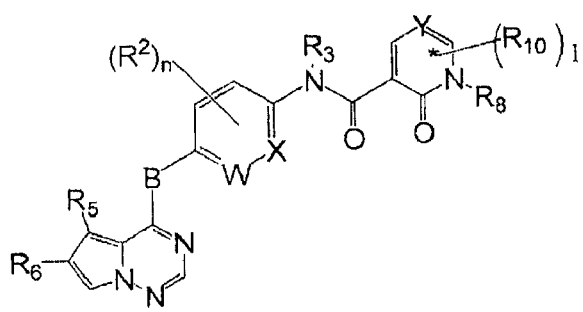

I
"
should read

--
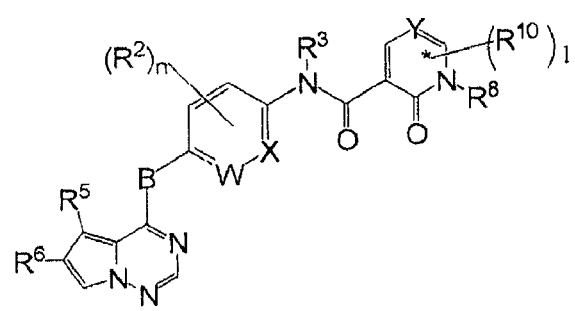

I
--

UNITED STATES PATENT AND TRADEMARK OFFICE
CERTIFICATE OF CORRECTION

PATENT NO. : 7,348,325 B2
APPLICATION NO. : 11/605168
DATED : March 25, 2008
INVENTOR(S) : Cai et al.

It is certified that error appears in the above-identified patent and that said Letters Patent is hereby corrected as shown below:

In Column 35, Lines 3-16,

"
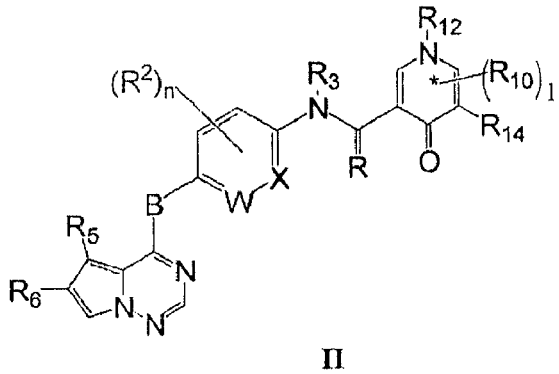

II
"

should read

--
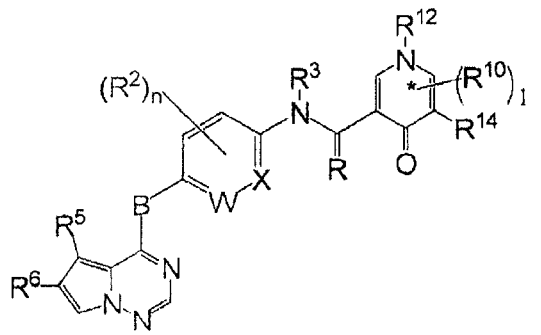

II
--

UNITED STATES PATENT AND TRADEMARK OFFICE
CERTIFICATE OF CORRECTION

PATENT NO. : 7,348,325 B2
APPLICATION NO. : 11/605168
DATED : March 25, 2008
INVENTOR(S) : Cai et al.

Page 4 of 5

It is certified that error appears in the above-identified patent and that said Letters Patent is hereby corrected as shown below:

In Column 36, Lines 4-5,

"HOF stimulation" should read --HGF stimulation--

In Column 36, Lines 11-36,

"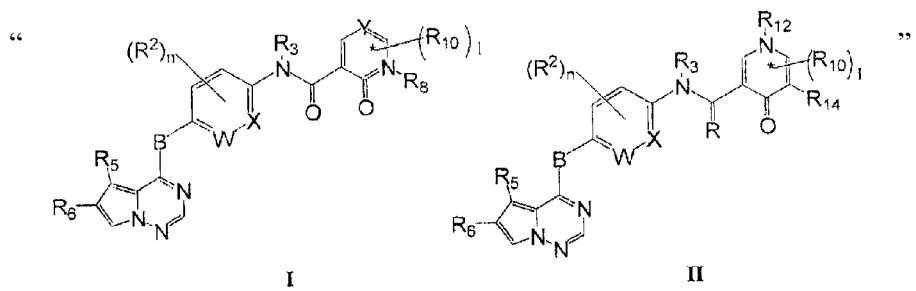"

should read

-- 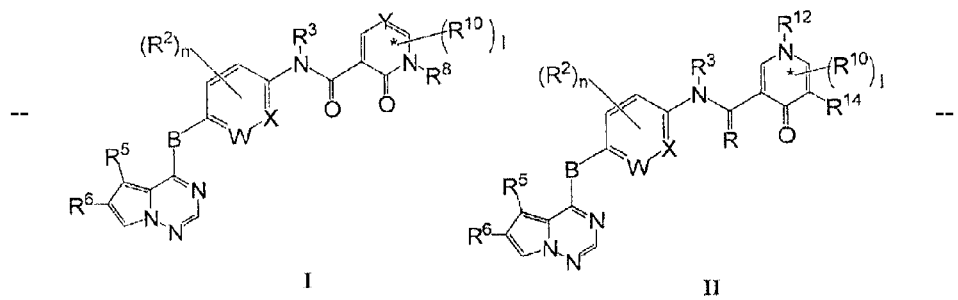 --

UNITED STATES PATENT AND TRADEMARK OFFICE
CERTIFICATE OF CORRECTION

PATENT NO.       : 7,348,325 B2
APPLICATION NO.  : 11/605168
DATED            : March 25, 2008
INVENTOR(S)      : Cai et al.

It is certified that error appears in the above-identified patent and that said Letters Patent is hereby corrected as shown below:

In Column 36, Line 55,
"substituted C6 to $C_{14}$ aryl" should read --substituted $C_6$ to $C_{14}$ aryl--

In Column 36, Line 59,
"substituted $C_1$ to $C^6$ alkyl," should read --substituted $C_1$ to $C_6$ alkyl,--

In Column 36, Line 63,
"$SO^2R^{51}$" should read --$SO_2R^{51}$--

Signed and Sealed this

Fifteenth Day of July, 2008

JON W. DUDAS
*Director of the United States Patent and Trademark Office*